US012082890B2

(12) United States Patent
Barnett et al.

(10) Patent No.: US 12,082,890 B2
(45) Date of Patent: Sep. 10, 2024

(54) SYSTEMS, APPARATUS AND METHODS FOR CONTINUOUSLY TRACKING MEDICAL ITEMS THROUGHOUT A PROCEDURE

(71) Applicant: Medline Industries, LP, Northfield, IL (US)

(72) Inventors: Samuel Benjamin Barnett, Northbrook, IL (US); David Noskowicz, Spring Grove, IL (US)

(73) Assignee: Medline Industries, LP, Northfield, IL (US)

( * ) Notice: Subject to any disclaimer, the term of this patent is extended or adjusted under 35 U.S.C. 154(b) by 0 days.

(21) Appl. No.: 18/385,573

(22) Filed: Oct. 31, 2023

(65) Prior Publication Data

US 2024/0065782 A1  Feb. 29, 2024

Related U.S. Application Data

(63) Continuation of application No. 17/348,563, filed on Jun. 15, 2021, now Pat. No. 11,925,422, which is a
(Continued)

(51) Int. Cl.
*A61B 34/00* (2016.01)
*A61B 90/00* (2016.01)
(Continued)

(52) U.S. Cl.
CPC .............. *A61B 34/25* (2016.02); *A61B 90/08* (2016.02); *A61B 90/361* (2016.02); *A61B 90/94* (2016.02);
(Continued)

(58) Field of Classification Search
CPC ....... A61B 34/25; A61B 90/08; A61B 90/361; A61B 90/94; A61B 90/96; A61B 90/98;
(Continued)

(56) References Cited

U.S. PATENT DOCUMENTS

2007/0268133 A1* 11/2007 Sanchez ............. G08B 13/2462
340/568.1
2018/0289428 A1* 10/2018 Lee ....................... G02B 21/365

* cited by examiner

*Primary Examiner* — Allen C Wong
(74) *Attorney, Agent, or Firm* — Fitch, Even, Tabin & Flannery LLP

(57) ABSTRACT

Systems, methods and apparatus are disclosed for improving medical procedures and medical procedure management, and, more particularly, for tracking medical instruments throughout a procedure and assisting medical personnel throughout the procedure or at least at the conclusion of the procedure. In one form, an apparatus for tracking medical instruments throughout a procedure is disclosed having a single camera for tracking movement and/or detecting position of a plurality of medical instruments during a medical procedure as at least one of the plurality of medical instruments is moved between multiple zones at least including a first prep zone and a second procedure zone. The apparatus having a controller connected to and collecting images from the camera, and a display in electrical communication with the controller and/or the camera for displaying medical instrument data pertaining to the movement and/or position of the plurality of medical instruments.

20 Claims, 13 Drawing Sheets

Related U.S. Application Data continuation of application No. 16/180,749, filed on Nov. 5, 2018, now Pat. No. 11,065,068, which is a continuation of application No. 15/804,345, filed on Nov. 6, 2017, now Pat. No. 10,154,885.

(60) Provisional application No. 62/511,718, filed on May 26, 2017.

(51) Int. Cl.
| | | |
|---|---|---|
| *A61B 90/94* | (2016.01) | |
| *A61B 90/96* | (2016.01) | |
| *A61B 90/98* | (2016.01) | |
| *G06K 7/10* | (2006.01) | |
| *G06K 7/14* | (2006.01) | |
| *H04N 7/18* | (2006.01) | |
| *H04N 23/63* | (2023.01) | |
| *H04N 23/69* | (2023.01) | |
| *G08B 21/24* | (2006.01) | |

(52) U.S. Cl.
CPC .............. *A61B 90/96* (2016.02); *A61B 90/98* (2016.02); *G06K 7/10366* (2013.01); *G06K 7/1413* (2013.01); *H04N 7/183* (2013.01); *H04N 23/63* (2023.01); *H04N 23/69* (2023.01); *A61B 2090/0806* (2016.02); *G08B 21/24* (2013.01)

(58) Field of Classification Search
CPC ........... A61B 2090/0806; H04N 23/69; H04N 23/63; H04N 7/183; G06K 7/10366; G06K 7/1413; G08B 21/24
USPC ......................................................... 348/143
See application file for complete search history.

FIG. 2A

SYSTEMS, APPARATUS AND METHODS FOR CONTINUOUSLY TRACKING MEDICAL ITEMS THROUGHOUT A PROCEDURE

CROSS REFERENCE TO RELATED APPLICATIONS

This application is a continuation of U.S. patent application Ser. No. 17/348,563, filed Jun. 15, 2021, which is a continuation of U.S. patent application Ser. No. 16/180,749, filed Nov. 5, 2018, now U.S. Pat. No. 11,065,068, issued Jul. 20, 2021, which is a continuation of U.S. patent application Ser. No. 15/804,345, filed Nov. 6, 2017, now U.S. Pat. No. 10,154,885, issued Dec. 18, 2018, and claims the benefit of U.S. Provisional Patent Application No. 62/511,718, filed May 26, 2017, all of which are incorporated herein by reference in their entirety.

FIELD

This invention relates generally to systems, methods and apparatus for improving medical procedures and medical procedure management, and, more particularly, to systems, methods and apparatus for tracking medical instruments throughout a procedure and assisting medical personnel throughout the procedure or at least at the conclusion of the procedure.

BACKGROUND

Medical procedures have evolved over time into very efficient and well-choreographed routines, often using pre-packaged surgical kits containing all instruments and equipment needed for the particular procedure at hand. However, these routines often involve numerous medical personnel working with a litany of different tools and pieces of equipment, often times in a relatively small or cramped space. This is true whether the procedure is being performed in a clinical setting or in a high-tech operating room. In such procedures and environments, one of the most difficult things to do is track all tools, equipment or items being used during the procedure to make sure all are accounted for at the end of the procedure and that none are left where they shouldn't be left.

Conventional systems exist to track various items throughout a medical procedure, but all have their own shortcomings. For example, smart sponge systems exist that track how many sponges have been used during a procedure, how many have been returned or discarded, and how many remain out and unaccounted for. Often these systems are blind systems that simply note when an item is unaccounted for and require medical personnel to use equipment, such as scanners to scan items being checked-out or used, and then items, such as wands with integral antenna, to waive over a medical procedure area (e.g., over a patient, over surrounding patient support surfaces (like bedding, gurneys, tables, etc.), surrounding equipment, personnel, etc.) to locate the unaccounted for item. This takes up valuable time and does not provide the medical personnel with any additional information that would be helpful in locating the unaccounted for item.

Often times, these systems are also limited to a particular item and/or only track a small portion of a medical procedure area. For example, some smart sponge systems consist of a cart that includes a waste receptacle or bucket. Such systems limit their product tracking to sponges alone and ignore the numerous other items utilized during a procedure (e.g., scalpels, scissors, tongs, gauze, mesh, etc.). They also only track what is checked out and what is returned to the receptacle and do not track the surrounding procedure area. As mentioned above, they provide an antenna wand to search the surrounding procedure area that is not being tracked, but that requires medical personnel to perform additional tasks and is different from actually tracking a procedure area.

Some conventional systems go beyond tracking sponges, but these systems often require medical personnel to apply machine readable labels on all items that are to be tracked, which is again labor intensive and adds more work for medical personnel, rather than reduces the steps they have to perform so they can focus on the procedure at hand and do so efficiently to make the best use of what often is very expensive high-tech operating room time. These systems often include interrogators that communicate with a base command unit to track a location of an object that has been marked with a machine readable label so that the item can be tracked. Less intelligent versions of such systems are also employed that simply use metal detection technology to detect if any item has been left behind in sensitive areas.

Even in instances where medical kits are provided with pre-marked or pre-labeled items so that they can be tracked easier, these systems limit the tracking to those items in the kit and not additional items that may need to be employed during a procedure. In such systems, the focus is again on tracking a limited number of items and the procedural area, and again, the system operates blind either simply notifying personnel of a missing item or requiring personnel to scan surrounding area to locate the missing item.

Another problem associated with conventional systems is that they often rely too heavily on computer readable indicia that can only be detected by the electronic equipment used by the medical personnel. This precludes the medical personnel from being able to do their own secondary check for redundancy purposes and can leave medical personnel feeling concerned after a procedure is concluded because they do not have their own way to independently verify or confirm instrument tracking was complete.

Accordingly, it has been determined that a need exists for systems, methods and apparatus for improving medical procedures and medical procedure management, and, more particularly, to systems, methods and apparatus for tracking medical instruments throughout a procedure and assisting medical personnel throughout the procedure or at least at the conclusion of the procedure.

BRIEF DESCRIPTION OF THE FIGURES

Embodiments of the invention are illustrated in the figures of the accompanying drawings in which:

FIGS. 2A-E are exemplary screen displays of a system or apparatus in accordance with embodiments of the present invention for improving medical procedures and medical procedure management, and tracking medical instruments throughout a procedure and assisting medical personnel throughout the procedure or at least at the conclusion of the procedure;

Elements in the figures are illustrated for simplicity and clarity and have not necessarily been drawn to scale or to include all features, options or attachments. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

Similar features shown in the different embodiments illustrated in the figures above share similar reference numbers. Each element has a three digit reference number, with the first digit representing the embodiment number and the last two digits representing the component. Other than the differences explicitly described and/or shown, elements with corresponding elements are understood to be substantially similar.

DESCRIPTION OF THE INVENTION

Many variations of system or apparatus for improving medical procedures and medical procedure management are illustrated herein. In some embodiments, the system comprises a medical procedure monitoring system capable of monitoring an entire medical procedure room and tracking all items used therein. In other embodiments, a medical procedure prep table or cart are disclosed which are capable of monitoring the prep table area and/or the entire procedural area. In yet other forms, custom procedural kits, drapes, patient supports and/or zone markers are disclosed which are equipped with items for improving medical procedures and medical procedure management in accordance with the inventions disclosed herein. While it is contemplated that these items will be provided to work with an overall system, it should also be understood that they may be provided individually and intended to work with third party zones, as may be desired.

Figure 1A:
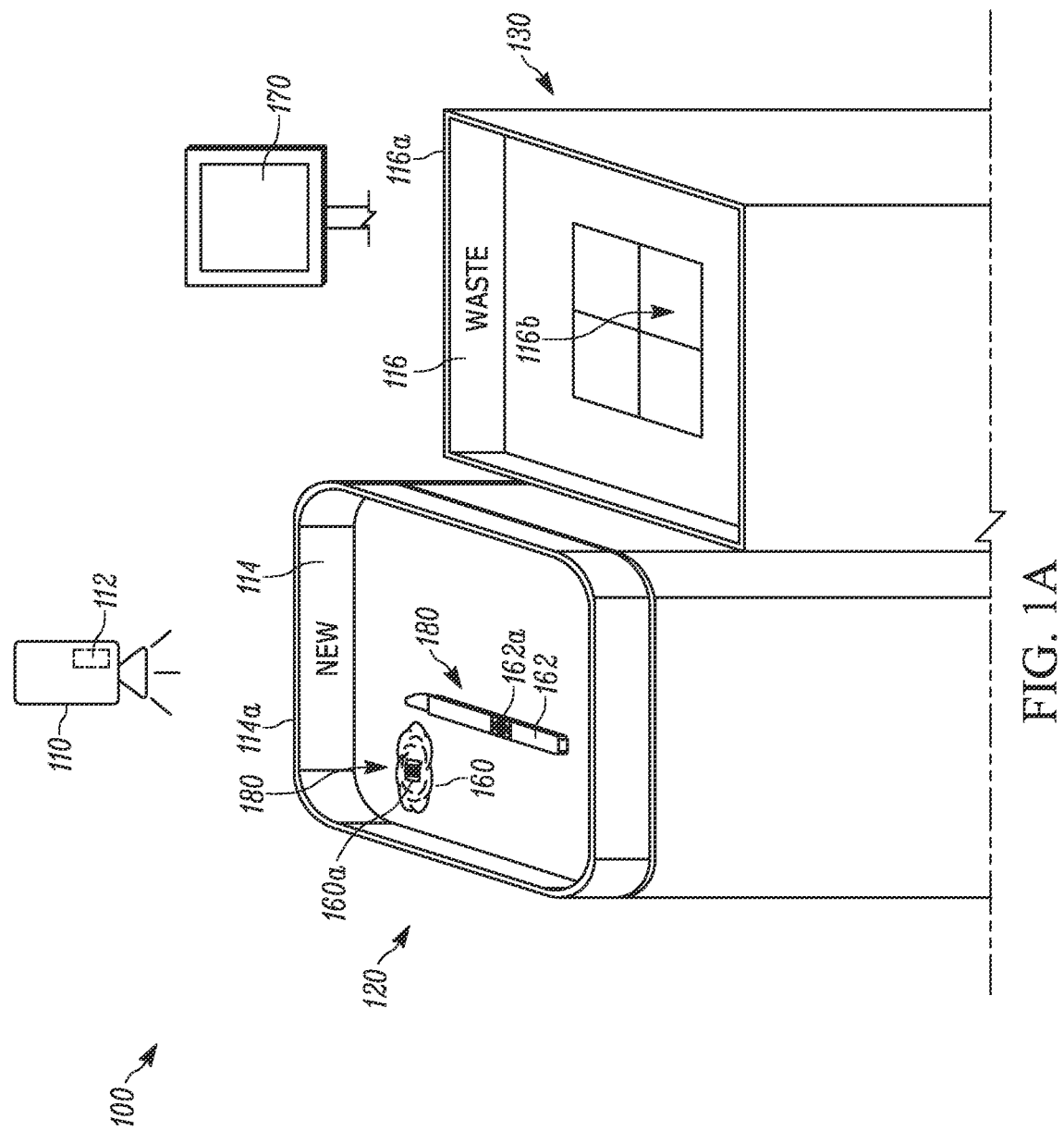
FIGS. 1A-1B are perspective and top views, respectively, of a medical procedure area and an exemplary system or apparatus in accordance with embodiments of the present invention for improving medical procedures and medical procedure management, and tracking medical instruments throughout a procedure and assisting medical personnel throughout the procedure or at least at the conclusion of the procedure.
Figure 1B:
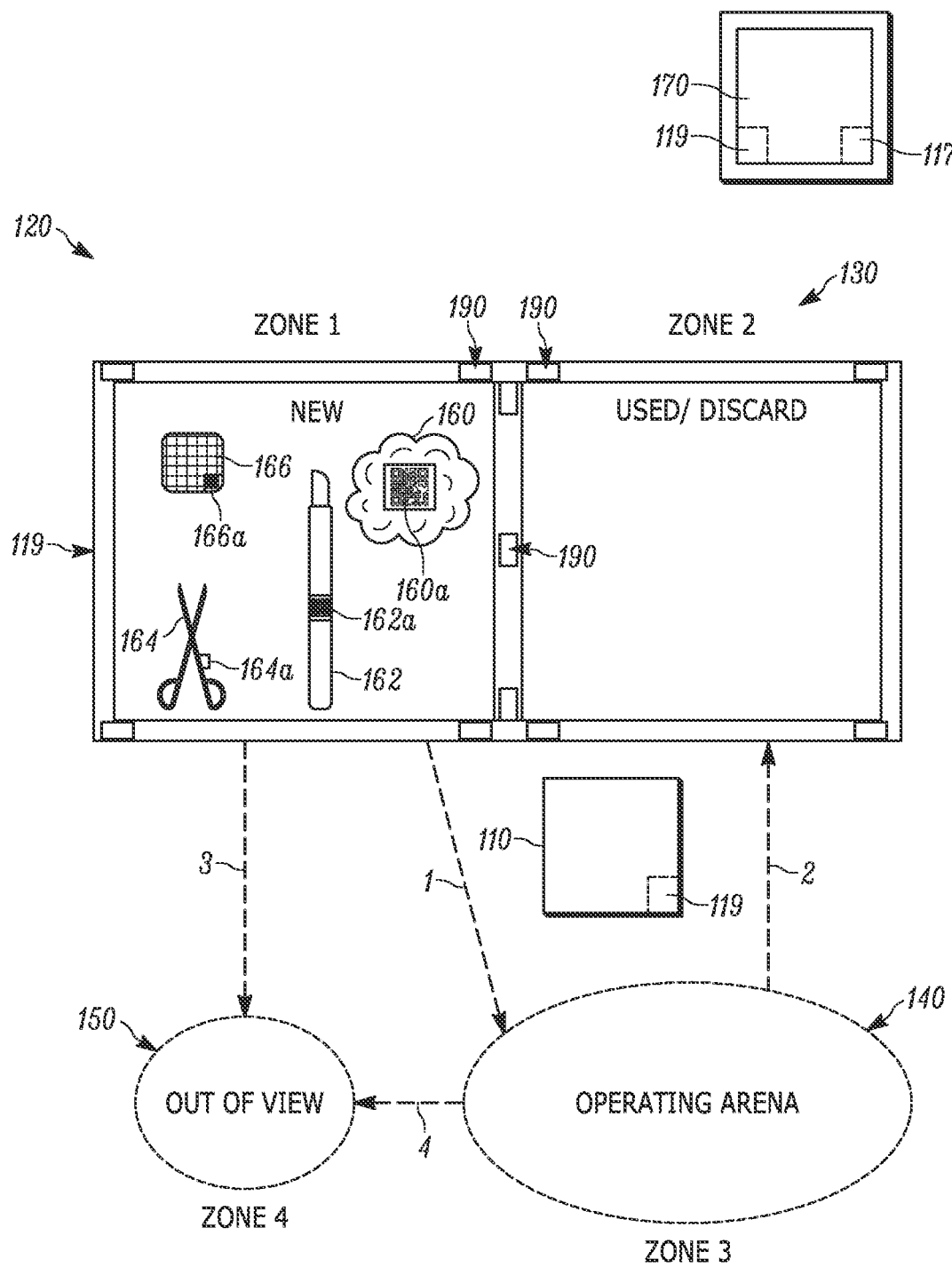

Turning first to FIGS. 1A-B, there is disclosed system or apparatus in accordance with embodiments of the present invention for improving medical procedures and medical procedure management, and tracking medical instruments throughout a procedure and assisting medical personnel throughout the procedure or at least at the conclusion of the procedure. The layout illustrated in FIG. 1A is slightly different than the layout in FIG. 1B in that FIG. 1A illustrates a single tray and a waste area, whereas FIG. 1B illustrates a tray with a starting instrument location and a used/discarded instrument location as well as other areas of the surrounding environment. While these embodiments differ slightly, they could be interchanged with one another and, thus, are treated such that common items use similar reference numerals. For example, in the forms illustrated, the system or apparatus are referred to generally by reference numeral 100 and include a camera 110 positioned for viewing a procedural area (e.g., whether that be limited to a prep table, a larger portion of the procedural area beyond just the prep table, the entire room, etc.) so that the system or apparatus 100 can track movement and/or detect positioning of a plurality of medical instruments during a medical procedure as at least one of the plurality of medical instruments is moved between multiple zones at least including a first prep zone and a second procedure zone. The system or apparatus 100 further includes a controller 112 connected to the camera 110 (e.g., in the instant embodiment it is integral to the camera 110, but could otherwise be connected remotely via a direct connection or a network connection, etc.) to collect images form the camera 110. In a preferred form, a display 170 will be in communication with the controller and/or the camera for displaying medical instrument data pertaining to the movement and/or position of the plurality of medical instruments via system or apparatus 100.

A variety of different types of cameras may be employed for camera 110, however, in a preferred form, system or apparatus 100 will only require one camera 110 for monitoring the desired procedural area, rather than requiring two or more cameras for monitoring specific portions of the procedural area (e.g., one camera for the prep table, another camera for the patient area, another camera for the waste receptacle(s), etc.). The camera 110 will be connected to the system or apparatus 100 via either direct connection via cable or wireless connection (e.g., RF transceiver setup, Wi-Fi, NFC, Bluetooth/BLE, etc.) or via a network interface which may also be wired (e.g., Ethernet, USB, etc.) or wireless (RF, Wi-Fi, NFC, Bluetooth/BLE, etc.). In the form shown in FIG. 1A, the controller 112 is located on the camera 110, however, in the form illustrated in FIG. 1B, the controller 112 is connected to or integrated into display 170. The camera 110 may either be permanently mounted or at least removably mounted in the procedural area (e.g., connected to the ceiling, light fixtures, existing medical equipment carts or towers, etc.), however, in alternate forms, the camera may be mounted to a mobile cart that is brought into the procedural area by the medical personnel and not left there permanently.

Similar to the camera 110, a variety of different displays may be employed for display 170. In a preferred form, the display 170 is a freestanding display that has wheels to make it mobile. However, in alternate embodiments, the display may be a component of equipment already contained in the procedural area (e.g., mounted to a wall, fixture, existing medical cart or tower, etc.), may be coupled to a mobile prep table that is moved into the procedural area when needed, and/or may be a remote electronic device, such as a smart phone or tablet computer. In some forms, the system or apparatus 100 may be app based and utilize a software application that is downloaded to a smart phone or other mobile device to interact with the remainder of the system or apparatus 100. In this way, users of the system (e.g., medical personnel), can utilize their own devices rather than having to bring in yet another component to a potentially already crowded procedure area. For example, in one form, the system 100 is equipped with a handheld scanner that is app based for scanning the surrounding environment to locate items identified as missing. The handheld device will preferably work in connection with the system 100 so that as the device is approaching the area where the missing device is detected the system will alert the user of his/her proximity to the missing item (e.g., such as by a visual que on display 170, an audible que provided by the system, etc.) in addition to the handheld device alerting the user to the proximity of the missing item (e.g., such as by providing another visual que on the display of the handheld or via the app, providing an audible que from the handheld, etc.). In still other forms, any one or more of such notification techniques may be utilized by the system to alert the user of the proximity of the missing item.

In the form illustrated in FIGS. 1A-B, the system or apparatus 100 is contained within the procedural area, however, it should be understood that in alternate embodiments, the system may connect to a remote central controller (e.g., a remote processing center, remote central server, remote central processing unit, etc.). In such instances, the remote central controller may be connected via a wide area network, such as the internet (e.g., cloud based, etc.) and located off-site or it may be located on-site and connected via a local area network or other conventional types of networks. The system or apparatus 100 may be setup with on-site equipment being configured in a fat or thick client configuration where the on-site equipment handles processing and rich functionality independent of the central server, or it may be setup in thin client configuration where the central server handles some or all of the processing of the data collected from the on-site equipment (or equipment located in the procedural area). It should be understood, however, that even if fat/thick client configurations are used, the system or apparatus 100 may be configured to relay data to a remote controller, such as a central server, in order for the data to be collected in a database and mined for relevant information. For example, the data may be used and/or analyzed to determine common traits behind the most effective procedures (e.g., best practices for specific types of procedures). It may be used to determine what instruments should be included in kits customized for certain procedures (e.g., so as to cut down on waste, etc.). It may also be used to rate medical personnel performance and/or facility performance (e.g., clinic performance, hospital performance, etc.). Another use may be for medical personnel in that the data may be used to determine what order a particular medical personnel or team (e.g., surgeon, surgical team, etc.) prefer to perform procedures in so that medical personnel tasked with prepping the procedural area can have the desired equipment ready to go in that order.

In the form illustrated in FIG. 1A, the procedural area includes a procedural instrument surface or tray 114 containing instruments required for the desired procedure, such as sponge 160 and scalpel 162. In a preferred form, the tray 114 will be a sterilized tray containing sterilized instruments (e.g., sponge 160, scalpel 162, etc.). The procedural area may also include a receptacle 116 for used or discarded instruments or waste in general. In a preferred form, the waste receptacle 116 includes flaps 116b that keep the contents of the receptacle 116 generally covered while new items are not being discarded. In FIG. 1A, the tray 114 and receptacle 116 are covered with sterilized drapes 118 to ensure that a sterile procedural environment is offered prior to and during the procedure.

The system or apparatus 100 will also preferably include instrument markers 180 and zone markers 190 which the system or apparatus 100 can use to identify an instrument and zone of the procedural area, respectively. The instrument and zone markers 180, 190 may take the form of any machine detectable or readable marker, such as bar codes, RFID sensors, alpha sequential markings, numeric sequential markings, alpha-numeric sequential markings, or just comprise a machine detectable image or shape. For example, in some forms, the instrument marker includes a bar code identifying the instrument and/or containing information about the instrument, such as a UPC, EAN, GTIN or other trade identification for identifying an item. In FIG. 1A, the instrument markers 180 are two- or three-dimensional (2D, 3D) hydrophobic barcodes that are preferably angle and/or orientation agnostic (meaning they can be read from any angle and/or orientation). In some forms, however, the instrument markers may only be detectable at angles that are between ±30° off normal (or from normal). In other forms, the instrument markers 180 are readable by system 100 over a range of angles that are at least between ±30° off normal (and preferably larger ranges of angles). In the form illustrated, the markers 180 are 3D markers that wrap around the instrument so that the system or apparatus 100 is capable of reading the marker 180 regardless of position or orientation (e.g., it is angle agnostic).

In a preferred form, the system or apparatus 100 will also utilize a marker that is also human friendly and not just computer detectable or readable. For example, the instrument or item markers 160a, 162a, 164a and 166a will also include a simplistic marking scheme that a human can also follow along and track instruments as a way of double checking and/or providing redundancy for the system or apparatus 100. In some forms, the markers may include an easy to follow sequential pattern so that a user can easily double check the instruments/items to confirm all are accounted for and can easily identify which is missing (if any). For example, markers may include a simple three letter visual que (e.g., AAA, AAB, AAC, AAD, etc.), that a human can follow to perform a redundant manual check to ensure all instruments/items are accounted for at the end of the procedure. This easy coded scheme can be based on alpha characters, numeric numbers, alpha-numeric combinations, or symbols (symbology). The latter could consist of simple imagery (visual symbolism) such as images of different fruits (e.g., apple, pear, banana, etc.), different shapes (e.g., circle, square, triangle, etc.), different images of commonly understood items (e.g., house, dog, car, different color crayons, etc.).

In a preferred form, the system or apparatus discussed herein will incorporate and embrace redundancy. For example, in preferred forms, the system or apparatus will include at least two of the following marking schemes for tracking instruments/items: machine detectable or readable marker; radio frequency identification (RFID); and/or an easy coded scheme that is readily human recognizable. The RFID markers may be active or passive RFID, however, in a preferred form, active RFID will be utilized. A benefit to the use of RFID markers over bar code markers is that they do not need to be within the line of sight for the reader to detect their presence which can be helpful in instances where the marker may not always be readily visible (e.g., medical personnel are holding the instrument in a way that hide or partially hide the marker, drape is folded over at least a portion of the marker, etc.).

In FIGS. 1A-B, the instrument markers 180 are preferably affixed to the instruments (e.g., sponge 160, scalpel 162). In the form shown, the instrument markers 180 are labels comprising a substrate with adhesive backing. Specifically, sponge 160 includes instrument marker label 160a, and scalpel 162 includes instrument marker label 162a. However, in other forms, the instrument markers 180 may be substrates or materials fastened to the instruments in a variety of other manners, such as by screw, bolt, rivet, hook and loop fastener, clasp or clamp, zipper and/or thread. In still other forms, the markers 180 may be bonded, etched, engraved, embossed, carved, molded, stamped, pressed, painted, printed or vapor deposited into/onto the instrument itself, or into/onto the marker material itself.

In FIG. 1A, the zone markers 190 are preferably made of a machine detectable indicia and may be used to divide at least portions of the procedure area into different zones. The zone markers 190 may be made in the same manner as the instrument markers 180, however, in a preferred form, the zone markers 190 do not need to be as complex as the instrument markers 180 in order to independently identify numerous instruments. Rather, they simply need to be machine detectable to identify the boundary of each zone and distinguish one zone from another. In FIG. 1A, the upper surfaces of the perimeter wall of tray 114 are lined with a first zone marker 114a to identify Zone One 120. Similarly, the upper surface of the perimeter walls of waste receptacle 116 are lined with another zone marker 116a to identify Zone Two 130.

In this way, system or apparatus 100 is capable of tracking the instruments 160, 162 as they are moved from the tray 114 identified as Zone One 120 to waste receptacle 116 identified as Zone Two 130. More particularly, system or apparatus 100 and, in particular, controller 112 uses camera 110 to track movement of instruments 160, 162 and can readily identify which zone the instruments 160, 162 are in when medical personnel want to know same.

In FIG. 1B, a slightly different tray 114 is used and is divided up between a new or sterile instrument side and a used or discarded instrument side. Such a tray may be used in situations where the instruments are not to be discarded (such as when they can be sterilized again and reused). In the form illustrated, zone markers 190 are applied around the upper perimeter wall and the central dividing wall of the tray to divide the tray 114 into Zone One 120 and Zone Two 130. In this exemplary embodiment, an additional zone, Zone Three 140, is used to identify the surgical arena, and another zone, Zone Four 150, is used to identify an area outside of the other zones and/or an area out of view of the camera 110. If desired, a waste receptacle, such as waste receptacle 116, could be added and another zone added for the waste receptacle by defining its boundaries with another zone marker, however, for simplicity such an additional item and zone is not shown in FIG. 1B at this time.

Thus, in practice, tray 114 may comprise a surgical kit customized for the particular medical procedure that is to take place and having zone markers 190 that divide the tray up into Zone One 120 and Zone Two 130, with Zone One 120 containing the necessary sterilized instruments for the intended procedure. The instruments illustrated are sponge 160 with sponge marker 160a, scalpel 162 with scalpel marker 162a, forceps 164 with scissor/clamp instrument marker 164a and gauze 166 with gauze marker 166a. In operation, system or apparatus 100 utilizes camera 110 and controller 112 to track movement of the instruments throughout the procedure from Zone One 120, Zone Two 130, Zone Three 140 and Zone Four 150. Thus, the system or apparatus 100 will track planned movement 1 of an instrument from Zone One 120 to Zone Three 140 where it will be used in the operating arena of the procedure area and planned movement 2 of the instrument from the surgical arena of Zone Three 140 to the discard or used region of Zone Two 130 on tray 114.

The system or apparatus will also track unplanned movement 3 of an instrument out of Zone One 120 (sterilized product area) to Zone Four 150 (area outside of the sterilized product area 120 or surgical arena 140) or unplanned movement 4 of an instrument out of Zone Three 140 (surgical arena) to Zone Four 150 (area outside of the surgical arena that is not one of the defined start or discard zones or is out of the view of camera 110). In a preferred form, the system or apparatus 100 includes an alarm 119 that will alert users (e.g., medical personnel) to the unplanned movement of one of the instruments 160, 162, 164 and/or 166. The alarm may be its own standalone component or it may be integrated into one of the other components of system or apparatus 100. In FIG. 1B, the alarm 119 is illustrated as being located in connection with either display 170 or camera 110. Preferably the alarm 119 will at least be associated with display 170 and will include both audio and visual components to definitively catch the eye of the user to alert them to the unplanned movement of at least one of the instruments. In some forms, the alarm 119 will include at least one of an audible alarm (e.g., audible sound or buzzer), a visual alarm (e.g., flashing light or change of color to stand out from surrounding portions of the screen, etc.) and/or a tactile or haptic alarm (e.g., a vibration, wobble, etc.), and in a preferred form, it will include all three.

In FIG. 1B, the system or apparatus 100 is configured to signal alarm 119 in order to indicate one or more of the following: a medical instrument is missing from all of the physical zones 120, 130, 140 and 150; a medical instrument is detected in an undesired zone (e.g., Zone Four 150, a used device approaching Zone One 120, etc.); a medical instrument detected in a zone for too long of a time period (or period of time); and/or a medical instrument moved out of a predetermined order established for the medical personnel involved. The first two examples immediately above indicating when alarm 119 should be signaled are clear, however, the latter three examples are a little less clear and show what can be done by the system or apparatus 100 being used to track performance over a plurality of procedures (e.g., based on prior data indicating best practices for the particular procedure itself, the preferred order of sequence for particular medical personnel involved in the instant procedure, etc.). For example, with the information that is gathered by system or apparatus 100 from prior procedures, the system or apparatus may learn or be programmed to understand that a particular instrument should only remain in a particular zone for a certain amount of time. If the system or apparatus 100 see an instrument in a zone for longer than the predetermined period of time, the system or apparatus 100 may immediately bring this to the attention of the users/ medical personnel so that a situation does not occur where this is only noticed at the end of a procedure (perhaps after a patient's operating opening is closed via staple or suture/ stitches).

In other examples, by being utilized in multiple procedures, the system or apparatus 100 may learn or be programmed to know the order that a particular procedure requires the instruments to be used in or the order particular medical personnel using the system or apparatus 100 like to proceed in and can tell when an instrument is taken out of order (or out of proper sequence) as it is being removed from the initial sterilized zone area of Zone One 120 and can alert medical personnel that an item is being taken out of the normal order instruments are used either for this procedure or for this particular medical personnel. In a preferred form, the system or apparatus 100 will detect movement of the instrument out of sequence while the instrument is still within the bounds of Zone One 120 and cause the return of the item without concern that it has been contaminated or is no longer sterile.

In still other forms, the system or apparatus 100 is capable of learning or being programmed to know what portion of the patient the procedure should involve and can monitor where the instruments are being taken and alert the medical personnel if they appear to be going to a portion of the patient's body that they should not be near. For example, if the procedure is an appendectomy and the system or apparatus 100 detects that instruments are being moved to the patient's left side (instead of right where the appendix is at) or if they are being moved toward the patient's shoulder, head, foot, etc., the system or apparatus 100 can alert the medical personnel so that a check can be made to ensure the proper procedure is being performed on this patient, that proper procedural steps are being followed, etc. In some forms, the system or apparatus 100 are synched with electronic medical records and is capable of knowing exactly what procedure is to be performed on the particular patient at hand and can alert the medical personnel if it appears to be taking action that does not correspond with the records provided for this patient (e.g., alerting personnel if they appear to be working on a right appendage when the records state that work is to be done on a left appendage, etc.). As should be understood by these examples, the system or apparatus 100 not only has the ability to make procedures more efficient and prevent errors associated with retained objects within a patient's body, but it also has the ability to double check and prevent erroneous procedures from being performed.

The examples immediately above are examples of artificial intelligence that the system or apparatus 100 can develop (e.g., learn or be programmed to know) over time and are referred to herein as procedural science. With this procedural science, system or apparatus 100 can assist medical personnel to perform procedures even more efficiently and can prevent undesirable conditions from presenting themselves or remaining present for long without at least alerting the medical personnel to same. That is not to say that the medical personnel may have a reason for the anomaly or atypical procedural tactics, but the system or apparatus 100 is at least capable of alerting the medical personnel to this issue and they can either correct the issue or use some form of actuator to at least temporarily clear or suspend the alarm condition. For example, an override switch may be included with system or apparatus 10. This could be a mechanical switch (e.g., push button, toggle switch, etc.) or it may be a software switch (e.g., an on-screen button, audible command, etc.). In a preferred form, however, the system or apparatus 100 will be configured to only allow the override to be set for a period of time and will then initiate the alarm again unless the alarm condition is no longer present. The actuation of such an override or suspend actuator will also preferably result in the system or apparatus 100 displaying on the display further information about the item that triggered the alarm condition (e.g., last location, position, velocity or speed of travel, vector or direction of travel and/or instrument marker data such as what marker data the medical personnel should be looking for in order to assist them in finding the missing item). In other forms, however, no override may be offered and the system 100 may prevent the procedure from proceeding until the missing item is located (e.g., such as by preventing the medical instrument retention alert system alarm from being disabled, preventing other systems from being operable until the missing item is found, etc.).

In addition, the system or apparatus 100 may include an active locator assistant that helps the user locate the missing item. For example, in some forms the active locator assistant projects a beam of light, such as a laser, to the last known location of the missing item. Further, the system or apparatus will preferably continuously track each instrument/ item and display on the display at least two of the x, y and/or z coordinates for the instrument/item, as well as specific data relating to both the spatial movement and position of the instrument/item. In some forms, the data provided will also include the zone the instrument/item is located within. Thus, system or apparatus 100 is capable of providing improved predictive analysis of where a missing instrument/item is likely to be should one go missing.

The system or apparatus 100 will include a user interface that the user operates to interact with the system or apparatus 100. Ideally all of the above mentioned actuators will be located on or accessible through the user interface. In the form illustrated, the display 170 includes a touch screen with a user interface including a button to locate missing instruments/items. In a preferred form, the user interface of display 170 will further include a button for activating the active locator assistant and another button for the alarm override. In alternate forms, however, the display and/or user interface may actually be app based and accessible through a smart phone or tablet. The system or apparatus 100 may be configured to display the buttons mentioned above at all times, however, in alternate forms, the buttons may only appear after an item has gone missing or may be accessed through an operating system having drop-down or cascading menus or windows. In the form illustrated, the user interface on display 170 will also provide an image of the missing instrument/item and allow a user to replay a clip illustrating the instrument/item prior to it going missing. In a preferred form, the system or apparatus 100 will capture and retain all video for the procedure so that the user will be able to determine how far back they want to go or how long of a clip they want to view of the missing instrument/item. This DVR like feature may be configured to retain the video of every procedure or it may automatically delete such video after a set period of time unless the user has selected or saved the video for retention beyond the date/time it would be deleted or overwritten by default practices. The system or apparatus 100 may store video data into local or remote memory storage that a user can access for replay to either review a procedure or track any of the plurality of medical instrument used during the procedure. This video data can be used along with the other procedural data collected (i.e., the procedural science) and utilized to critique medical personnel performance, identify mistakes, and/or identify best practices.

In addition to the above, the procedural science gained by repeated use of system or apparatus 100 can be paired with additional data relating to the procedure or patient (e.g., follow-up date regarding the patient such as if they had any setbacks, if they had to be treated for certain issues down the road that may have resulted from the way the procedure was performed due to it being a common issue for those going through the same procedure, etc.) to help identify best practices, particular medical personnel that excel in a particular procedure, etc. For example, it is now known that early appendectomies performed via laparoscopy with one incision going through the umbilical cord have resulted in a greater risk of umbilical hernias for these patients. It is possible that system or apparatus 100 would have been able to detect that sooner by pairing the data it collects from being involved in numerous procedures and pairing that with post procedure data relating to these patients.

Turning now to FIGS. 2A-E, exemplary screen displays of a system or apparatus in accordance with embodiments of the present invention are illustrated therein. As mentioned above, items similar to those discussed above with respect to FIGS. 1A-B will utilize the same latter two digit reference numeral, but have the prefix "2" instead of "1" to distinguish one embodiment from others. Thus, in the form illustrated in FIGS. 2A-E, the display is identified via reference numeral 270 and is similar to the exemplary displays discussed above with respect to display 170 in FIGS. 1A-B. In FIGS. 2A-E, display 270 illustrates a display screen that has camera images 271 located in an upper portion of the display 270 and the following camera images of the procedural area are illustrated (from left to right): tray camera image 271*a*, surgical arena camera image 271*b*, missing Zone Four tray camera image 271*c* and discard camera image 271*d*.

Below camera images 271 on display 270 are fields relating to the various zones being monitored by system or apparatus 200. From left to right, the display 270 illustrates tray Zone One field data 272, surgical arena Zone Three field data 273, missing Zone Four field data 274 and discard Zone Two field data 275. Although the camera images 271 are aligned with the specific zones that correlate with those camera images, it should be understood that in alternate embodiments, this may be arranged differently if desired. For example, the camera images could be arranged in a different order than the columns containing the zone data or zone information portion of the display (e.g., 272, 273, 274, 275). In other forms, the camera images may be aligned with their respective column zone data, but may be a different order than that depicted in FIGS. 2A-E. For example, the system 200 may be configured to allow the user to select what order these items appear or are presented on display 270. In still other forms, not all camera pictures need be displayed and/or the system can be configured to allow the user to select which pictures or column data appears on display 270 and in what order or position in order to allow the user to customize the layout to his/her preference or need. For example, it may be desirable to only display one of the zones (e.g., surgical arena) during the procedure and reserve the other images should a need arise to locate a missing item.

Figure 2A:
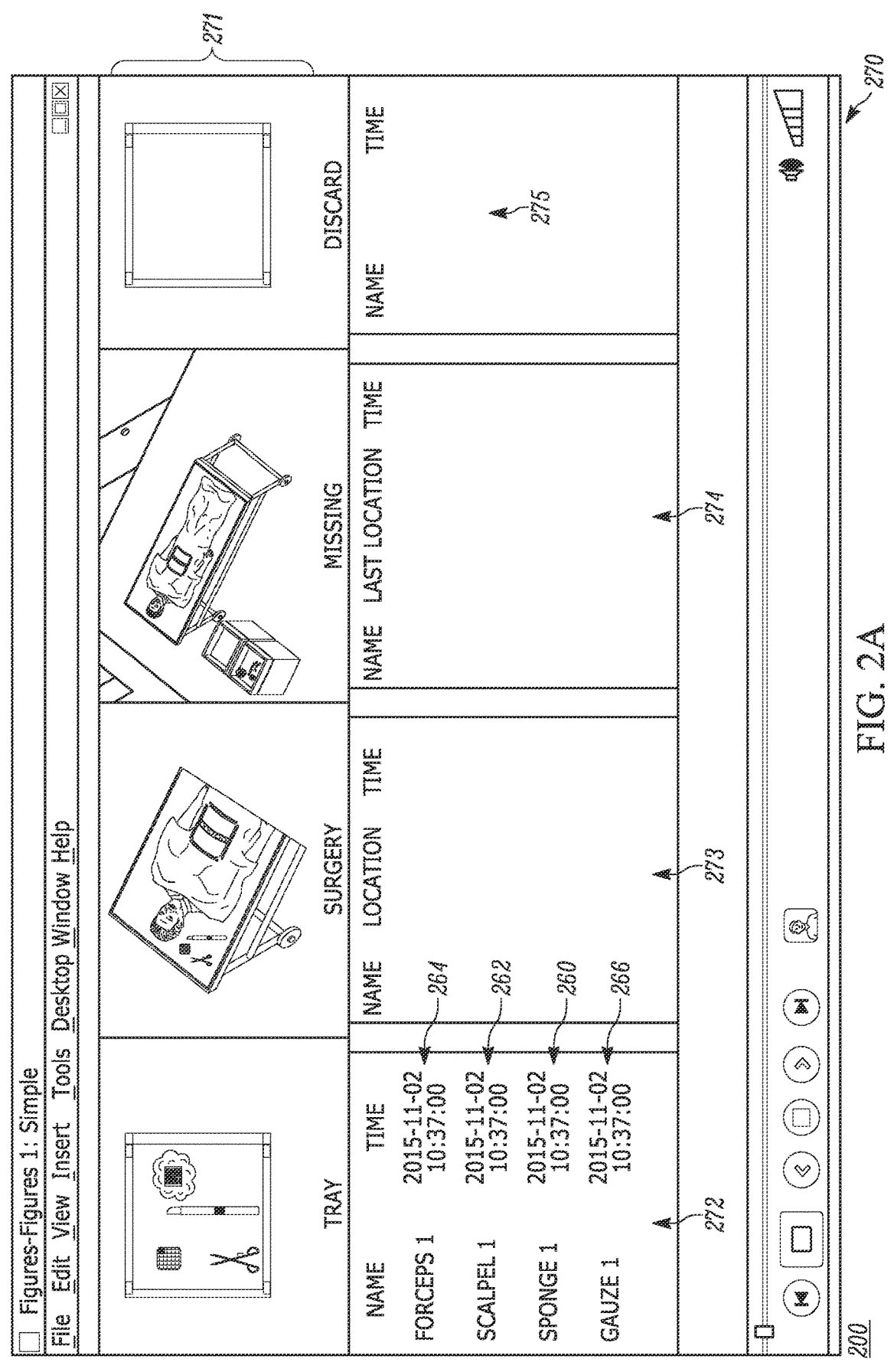
Figure 2B:
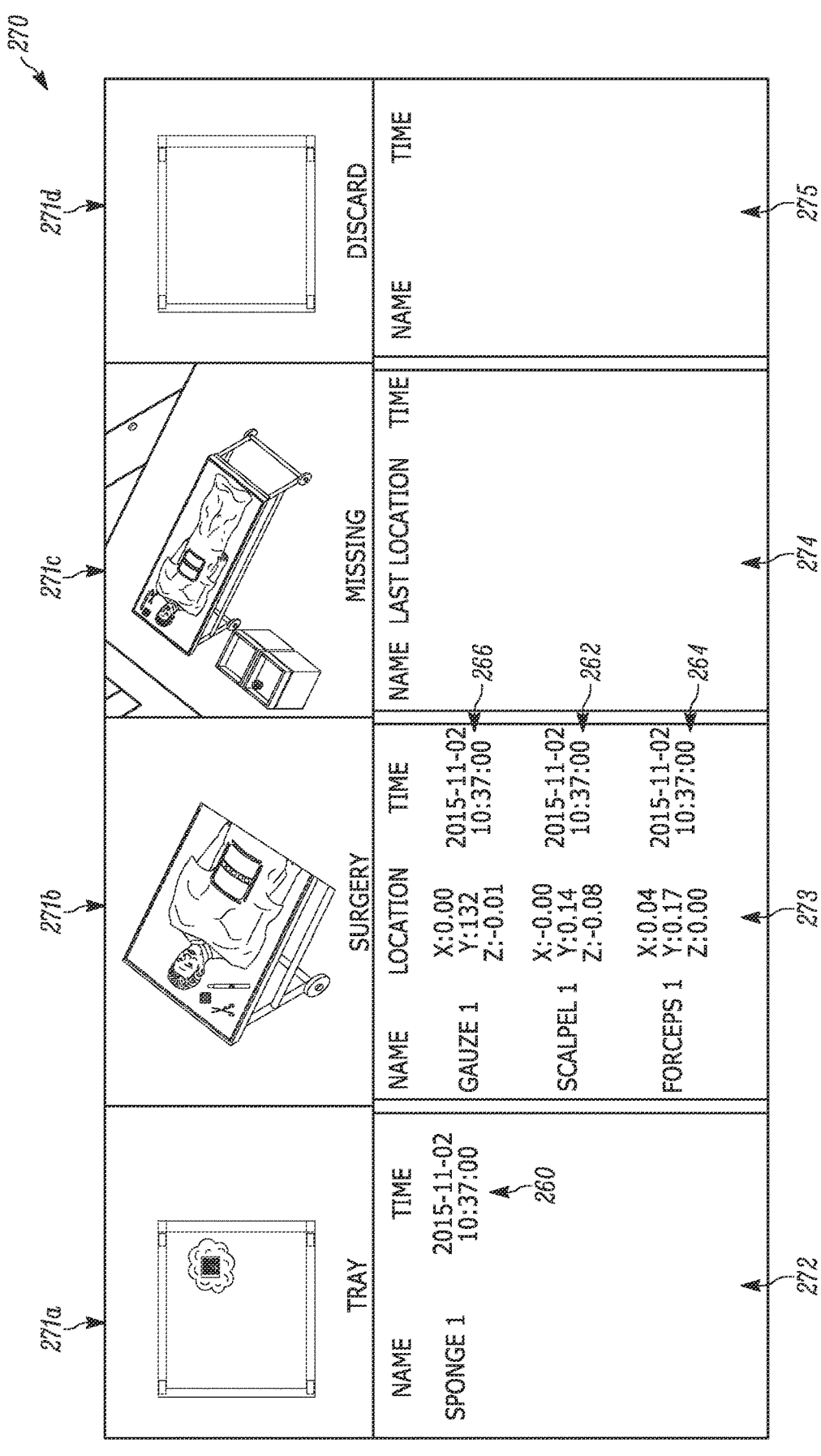
Figure 2C:
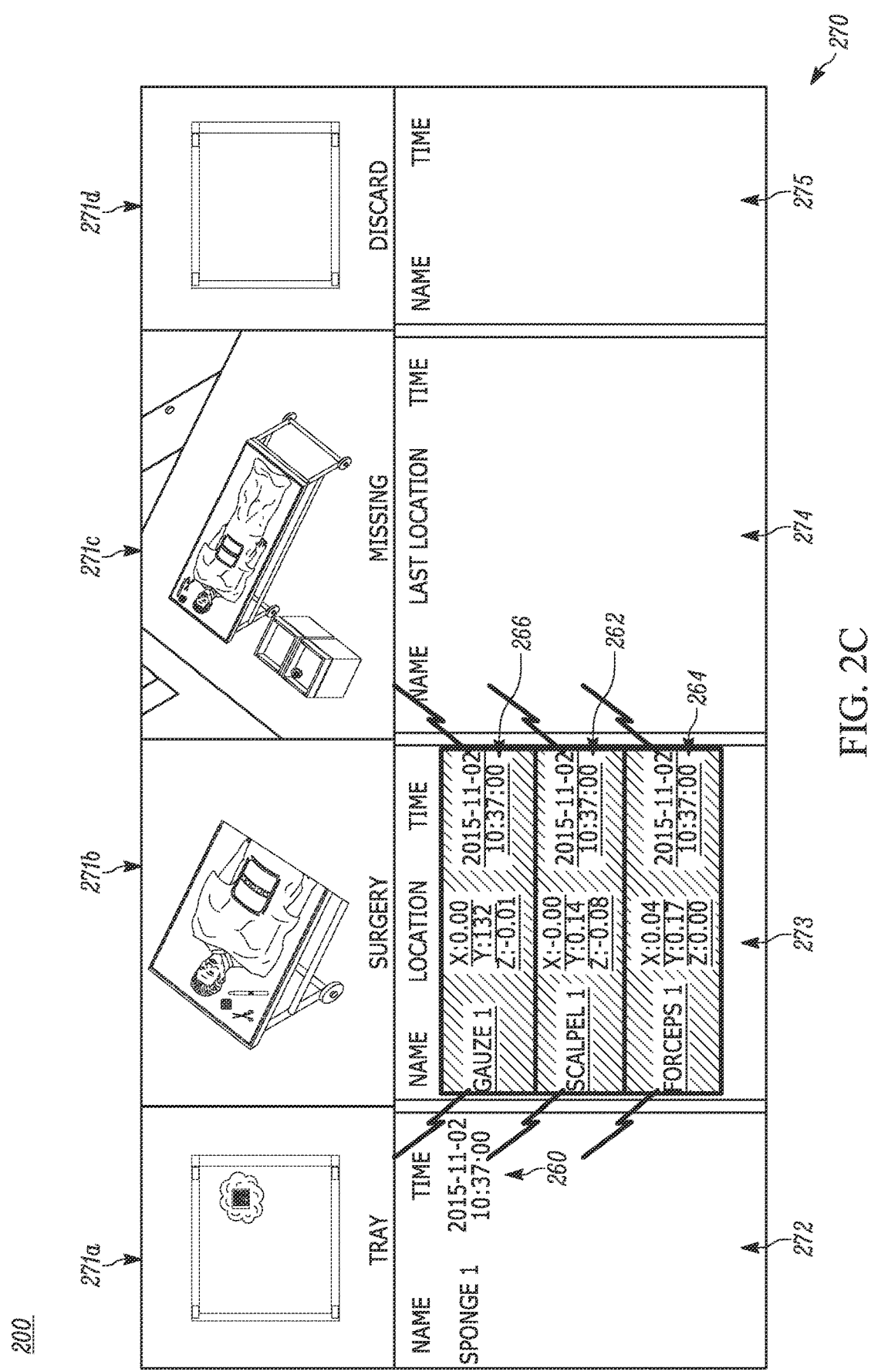
Figure 2D:
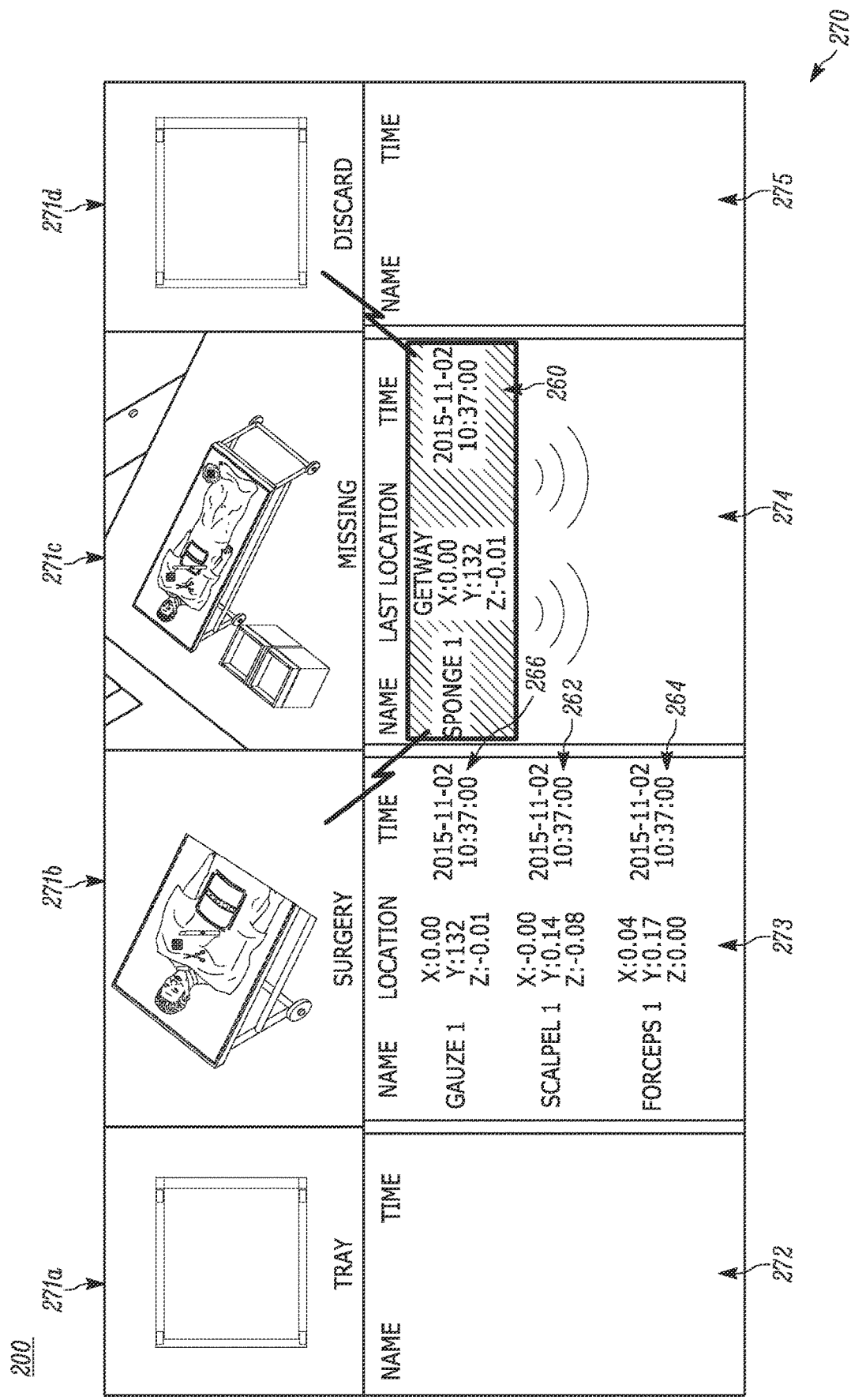

In a preferred form of operation, FIG. 2A illustrates the appearance of display 270 at the start of a medical procedure where all of the instruments (e.g., forceps 264, scalpel 262, sponge 260 and gauze 266) are located on tray 214 (illustrated in tray camera image 271*a*) are identified as being in the tray 214 as illustrated by the tray status field 272. In FIG. 2B, the gauze 266, scalpel 262 and forceps 264 have been moved from the tray 214 to the procedure area or arena (or surgical area/arena) zone 240 as illustrated in tray camera image 271*a* and surgical arena image 271*b*. In a preferred form, as items or instruments are moved from one zone to another, the display 270 will highlight those items or instruments in a color, such as the red or pink color illustrated in surgical arena zone 273 in FIG. 2C to make it clear to users that these items have recently moved into this zone. The system 200 could be configured to keep the items highlighted in color the entire time they are outside of the tray image 271*a*, or it could be configured to simply highlight them in a color once when they move to a new camera image or field. In a preferred embodiment, the items will be highlighted in color and blink in column 273 while the item is detected in the surgery camera image 271*b* and stop blinking when returned to the tray image 271*a*/column 272 or the discard image 271*d*/column 275. The jagged lines (or lightning bolts) under column 273 in FIG. 2C are meant to represent the flashing of the red or pink color for the items detected in the surgery camera image 271*b* If an instrument/item is removed from one of the acceptable zones (i.e., tray Zone One 220, procedure Zone Three 240 or discard Zone Two 230), such as movement of the instrument/item to missing Zone Four 250, then the system or apparatus 200 will display the missing item under missing item field 274 as illustrated in FIG. 2D. As mentioned above, in a preferred embodiment, this instrument/item will be highlighted in color to draw attention to same from the user, but it will also preferably be accompanied by an alarm alerting the user to the fact an item is missing. In the form illustrated, the alarm sounds an audible beep or tone followed by an audible announcement announcing the name of the instrument/item missing. In the form illustrated in FIG. 2D, the jagged lines represent that the highlighted color flashes to draw attention to the missing item and the arced lines represent the audible alarm or alert that will preferably play. In a preferred form, the items are highlighted in a flash of color once when moved from the tray field 272 to the procedure area 273, but are repeated highlighted in flashing color in missing field 274 if they have gone missing. In alternate forms, more or less flashing of color may be used or none at all. For example, in some alternate forms, the highlighting of the items in color may be reserved for only when those items have gone missing and show-up in field 274.

Also as mentioned above, the system or apparatus 200 will preferably be equipped with an override actuator that the user may actuate if the item has been intentionally moved out of the main zones. Ideally, the alarm will only be delayed by a period of time (which may selected by the user or, alternatively, may be predetermined by system or apparatus 200) so that the override operates more like an alarm clock's snooze button, rather than completely disabling the alarm. However, in other forms, the system or apparatus 200 may be provided with an override that completely overrides the alarm or it may be provided without an override. Given that the system's alarm will preferably be using audible alerts, in preferred forms the system or apparatus 200 will include an override (e.g., snooze, sleep or mute actuator) in order to prevent the audible alarm from creating an unnecessary commotion in the procedure area.

Figure 2E:
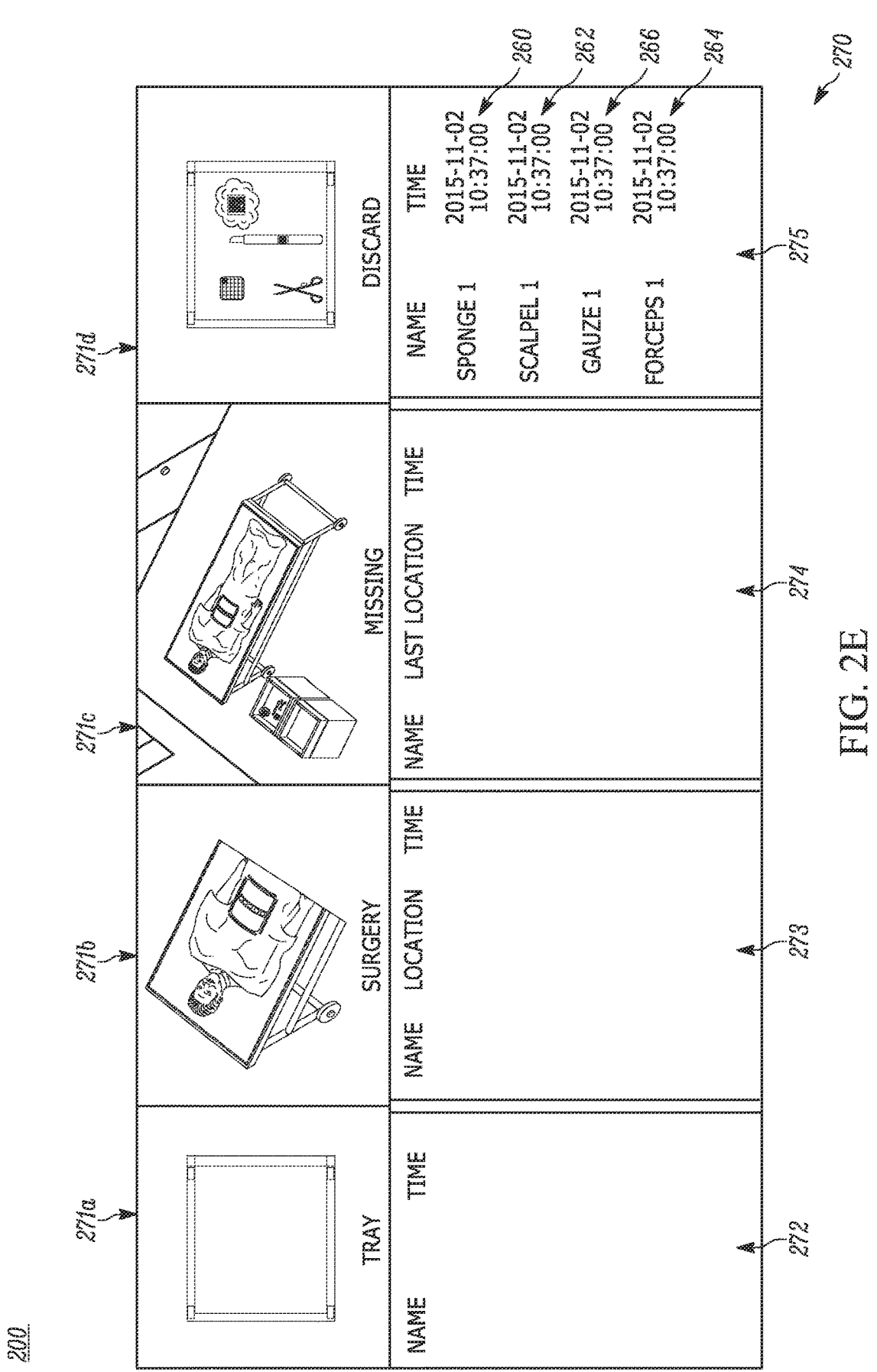

Once all instruments/items are returned to the discard Zone Two, the display 270 will illustrate same in discard Zone Two field 275 and all alarms (if any) will be disabled as illustrated in FIG. 2E. Although the embodiment illustrated in FIGS. 2A-E, illustrates that all the instruments/items are returned to a single zone or location, such as discard Zone Two 230 as illustrated in camera image 271*d* and discard zone field 275, it should be understood that in alternate embodiments instruments/items may be returned to one or more zones or locations as desired. For example, in embodiments where a tray with a discard portion is provided for items that can be sterilized and reused and a trash receptacle is provided for items that cannot be reused, it may be desirable to have system or apparatus 200 configured to direct users to return the reusable items to the discard portion of the tray and the non-reusable portions to the waste receptacle. If the user fails to do this, the system or apparatus 200 could be configured to notify the user of this and/or trigger an alarm until such steps are complied with.

In a preferred form, the system or apparatus 200 will be able to display on the display 270 additional information relating to any instrument and can be configured to do this at all times or only during alarm conditions. For example, the tracking system or apparatus makes it possible to not only identify what zone a missing instrument was last in, but it will preferably also be able to provide x, y and z coordinates for same. Other information it may provide include beyond location or position include velocity or speed of travel, vector or direction of travel, telemetry and/or instrument marker data. The system 200 will preferably be able to provide x, y, z coordinates for items while the items are in use (even if not missing) and provide time stamp data or time tracking information for each item. This data may be useful for training of medical professionals, such as by showing how instruments were used and/or for how long in procedures that went well, those that did not go well or as desired, or in a comparison and contrast between those that went well and those that did not go well or as desired.

In FIGS. 2A-E, the video images depicted in image row 271 will show realtime imagery of the specific areas or zones they are monitoring. For example, in FIG. 2A, all instruments for the procedure being performed are shown in the tray in image 271*a* and tray field 272. Once the procedure has begun, the items that are moved to the procedural area are shown in surgery image 271*b* with those remaining in the tray still being shown in tray image 271*a* as illustrated in FIG. 2B. The initial movement of the items (e.g., from the tray to the procedural area) is emphasized by highlighting the items that were or are being moved in color as illustrated in FIG. 2C. In a preferred form, these items will continue to blink in the highlighted color while in use during the procedure, however, in alternate forms, the highlighted blinking may only be used upon the initial movement of the item away from its starting position. Once the items are returned to the desired discard area (e.g., tray, waste receptacle, etc.), the items will be shown in the procedure conclusion field 275 as illustrated in FIG. 2E without any highlighting via color. In a preferred form, an audible tone or announcement will also be made to confirm to the medical personnel that the item has properly been recorded in or detected in the discard area. Again, while the camera image 271*d* in FIG. 2E shows all items returned to the discard area, it should be understood that in other forms of the invention some items may be shown returned to a discard area or tray for later sterilization while others are confirmed having been thrown away in an appropriate receptacle, such as by detecting the item within the zone markers delineating the waste receptacle opening and/or not detecting it leave that delineated boundary.

Should an item go missing during the procedure, such as out of the sight or zone of the tray camera image 271*a*, procedural camera image 271*b* and/or discard camera image 271*d*, the missing item will be moved to missing field 274 and preferably highlighted in a flashing color with the audible alert being sounded for same as illustrated in FIG. 2D. In a preferred form, the system will announce the item that is missing (e.g., "Missing forceps 1", "missing sponge 1", etc.). In a preferred form, the missing item camera image 271*c* will be setup to show where the missing item is if visible. For example, in FIG. 2D, the sponge 260 is shown as having gone missing from the image areas of 271*a*, 271*b* and 271*d*, but is illustrated down at the foot of the patient in missing item camera image 271*c*. In some forms, the system will be setup to automatically replay a video clip in missing item camera image 271*c* showing where the missing item was last seen or detected right before it went missing and the data illustrated in missing field 274 will display the x, y, z coordinate and time data for the item's last detected location and preferably the vector data (e.g., velocity and trajectory/direction data) of the item at that time to give an idea of where it may be. In other forms, the system may require the user to select an item (e.g., physically depress or actuate a button, touch a software button such as GUI interface or icon on display 270, etc.) to get the video clip to play and simply will display the missing item camera image 271*c* showing a larger view or zoomed out view of the room within which the procedure is taking place or surrounding environment around where the procedure is taking place beyond those areas depicted in the other camera images 271*a*, 271*b* and 271*d*.

Figure 3:
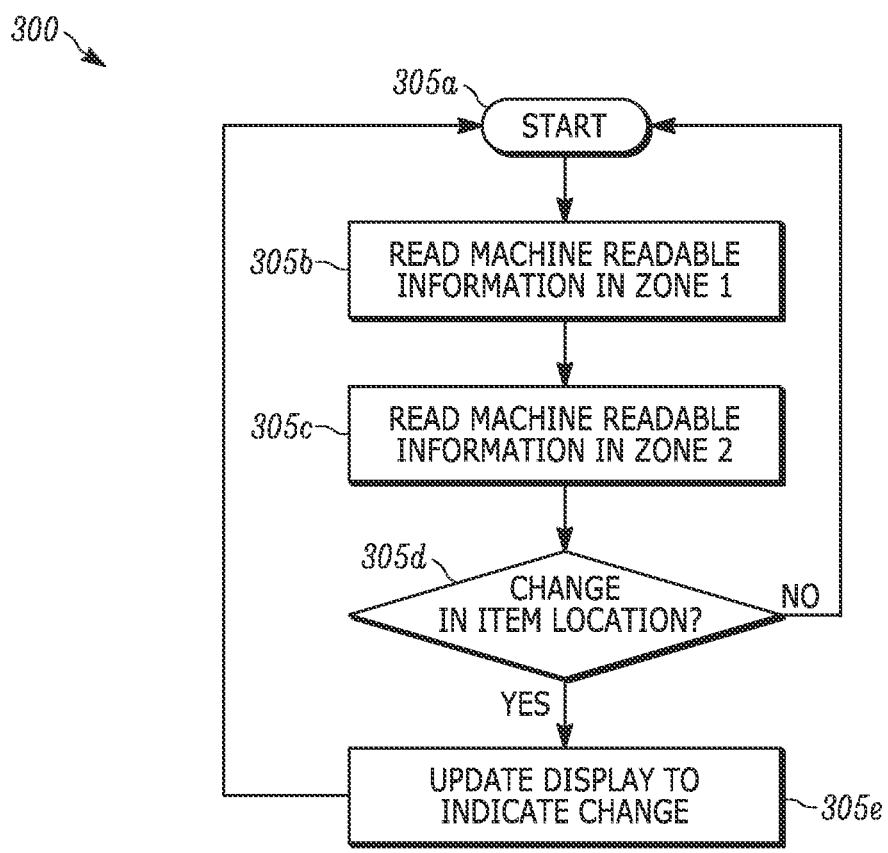
FIG. 3 is a flow chart illustrating an exemplary process a system or apparatus in accordance with embodiments of the invention may follow for improving medical procedures and medical procedure management, and tracking medical instruments throughout a procedure and assisting medical personnel throughout the procedure or at least at the conclusion of the procedure.

FIG. 3 is a flow chart illustrating one manner in which the system or apparatus may be configured to run. In a preferred form, the controller of system or apparatus 300 would include a process configured to perform the following steps or process. The process would start at step 305*a* and use the camera to detect machine detectable data (e.g., read machine readable information) in tray Zone One 305*b*. Then the system or apparatus 300 would detect machine detectable data (e.g., machine readable information) in discard Zone Two 305*c*. Next, in step 305*d*, the system or apparatus 300 would determine if a change in an instrument/item location has occurred. If not, the program would return to start 305*a*. If so, the system or apparatus 300 would update the display to indicate the detected change in step 305*e*. As mentioned above, in a preferred form, the system or apparatus 300 will actually highlight the instrument/item once it has changed from one zone to another in order to make it easy for the user to see the change that has taken place.

Figure 4A:
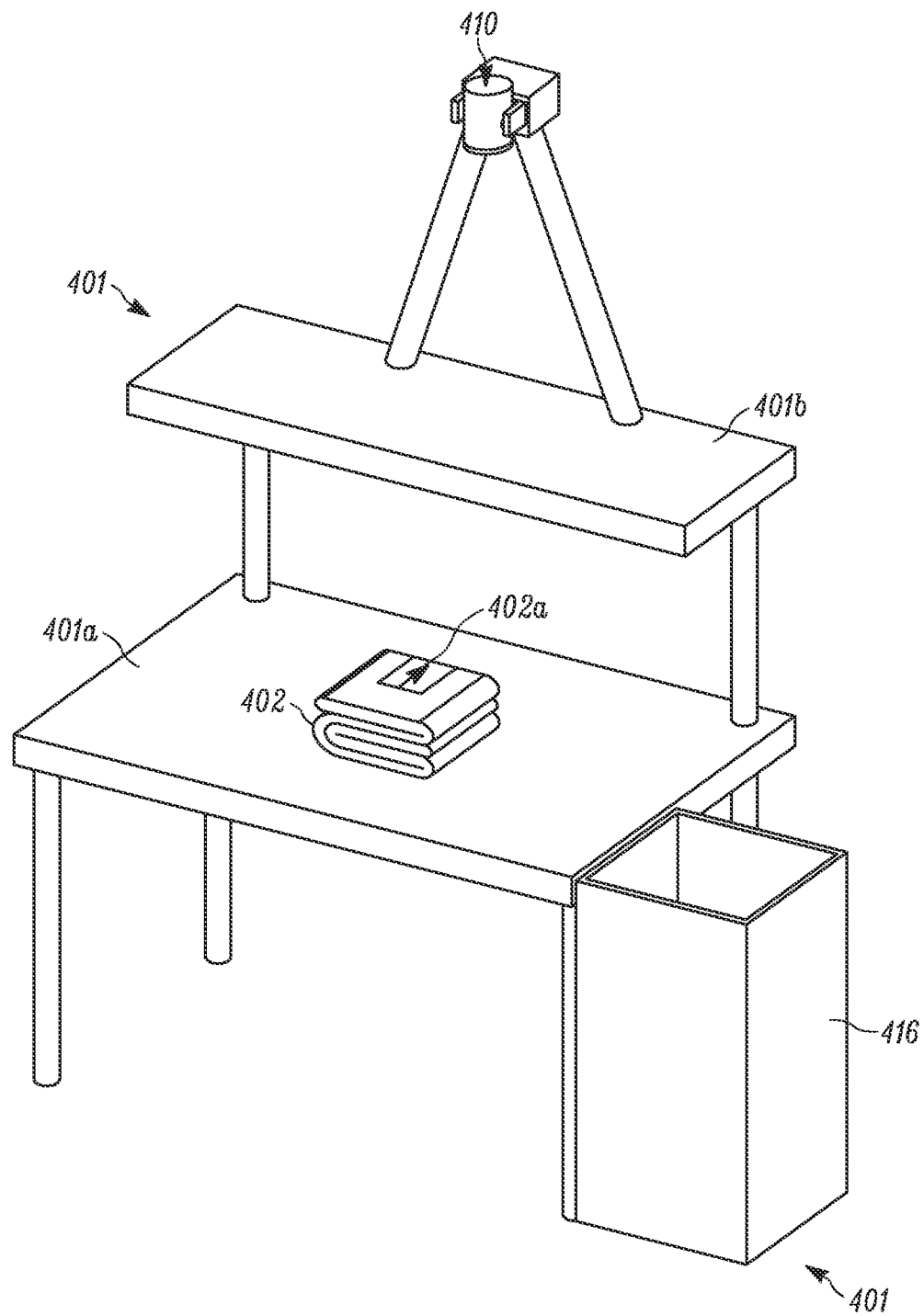
FIGS. 4A-C are perspective views of a procedural prep table and/or drape for same in accordance with embodiments of the invention, with FIG. 4A illustrating a folded drape having integral directions for installation and integral machine detectable indicia for use with the systems and apparatus discussed herein, FIG. 4B illustrating the drape partially unfolded on the prep table, and FIG. 4C illustrating the drape completely unfolded (or fully deployed/installed) on the prep table in accordance with embodiments of the invention.
Figure 4B:
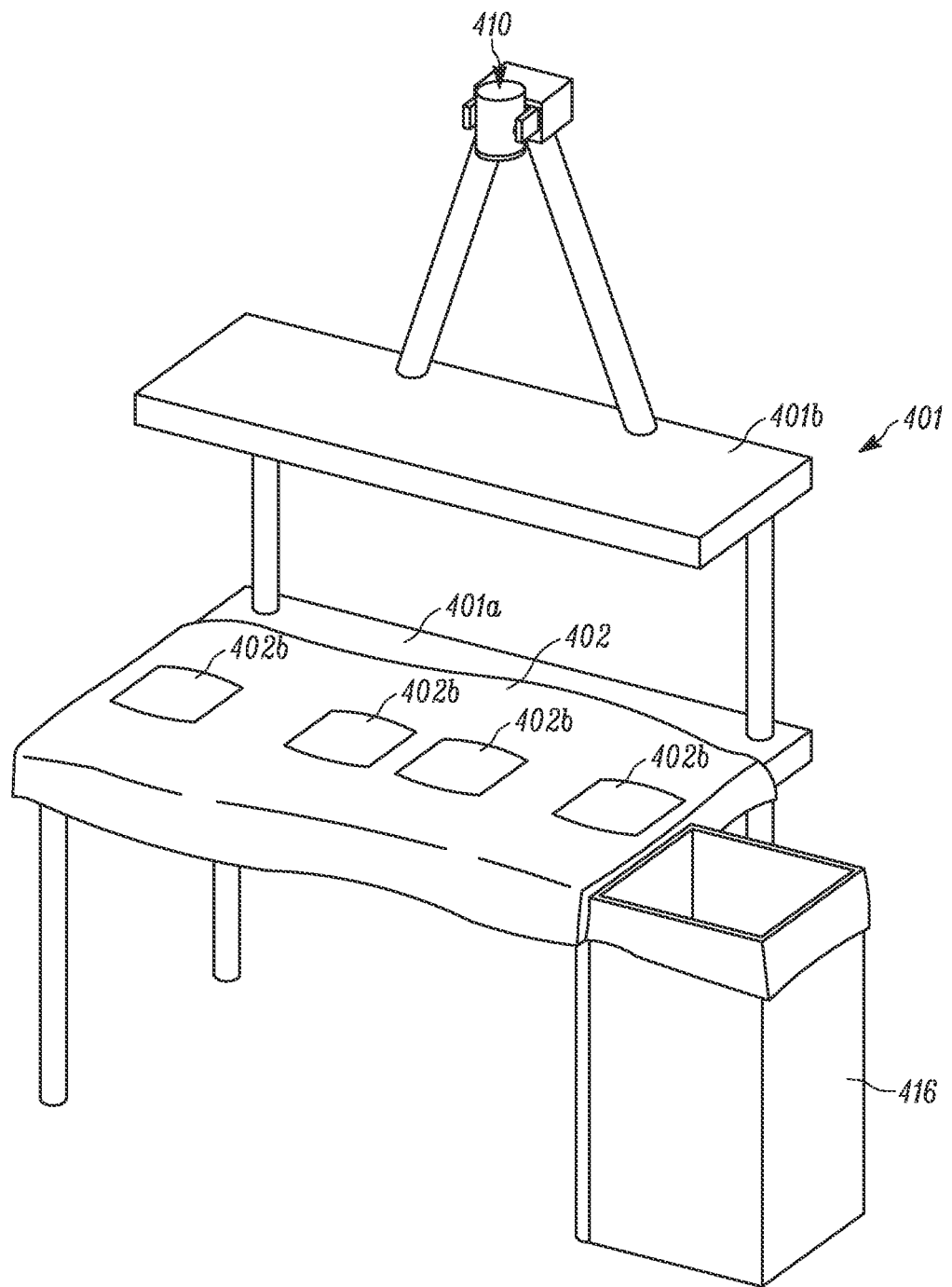
Figure 4C:
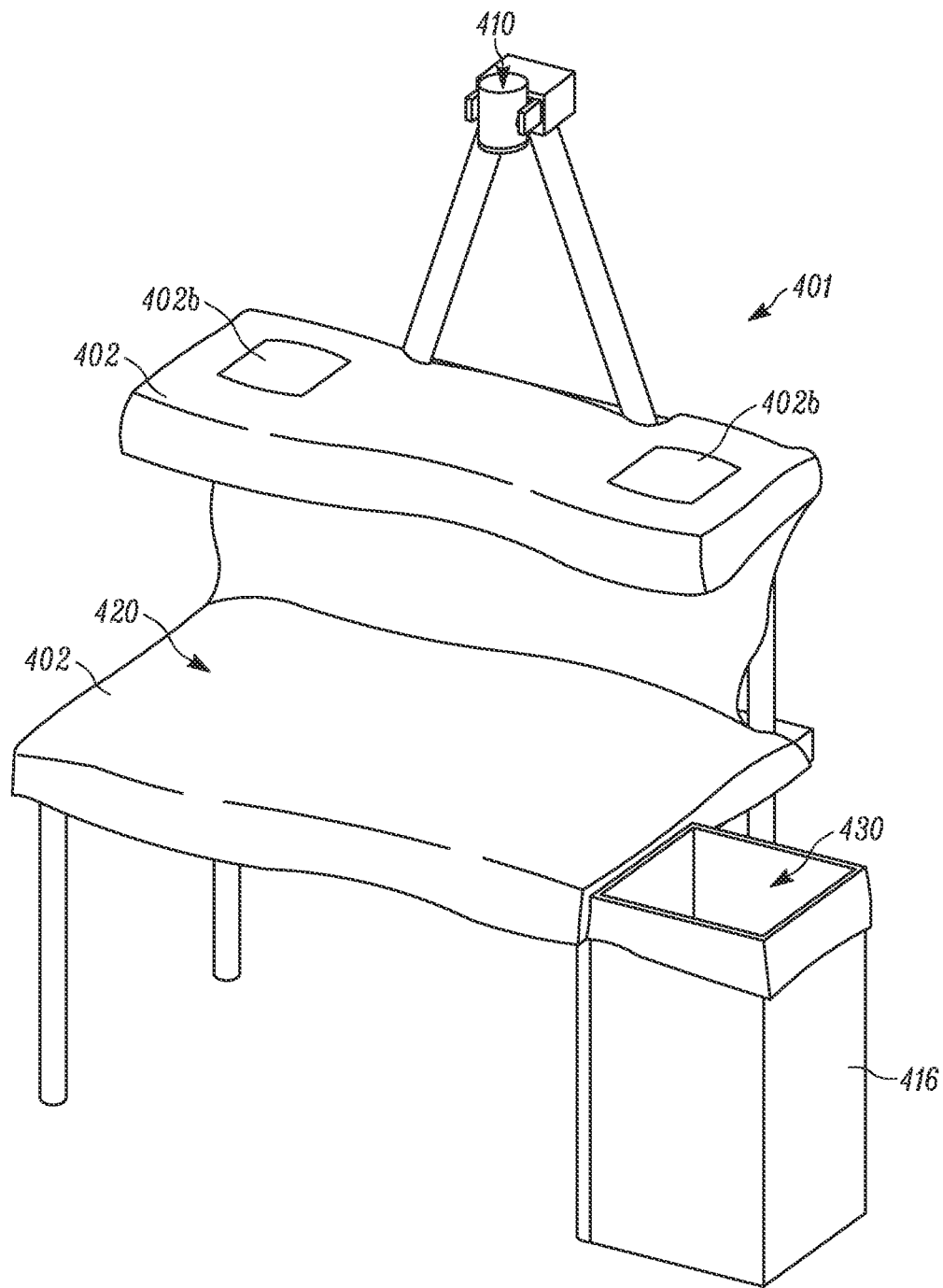

In FIGS. 4A-C another exemplary embodiment in accordance with the invention is illustrated showing a system or apparatus 400 comprising a procedure prep table 401, having a first shelf 401*a*, second shelf 401*b*, camera 410 and waste receptacle 416. In the form illustrated the prep table 401 is shown as a stationary table that rests on four legs, however, it should be understood that in alternate embodiments the prep table 401 could be a mobile table, such as one having casters or wheels on the bottom of each leg (preferably lockable). In the form shown, the system or apparatus 400 includes a prep table drape 402 that is sterilized and capable of being unfolded to cover all prep table surfaces to provide a sterilized surface upon which to rest equipment/items to be used during the medical procedure. In FIG. 4A, the prep table drape 402 is shown in a folded state as it appears once removed from its initial packaging. In a preferred form, the drape 402 includes integral instructions 402*a* explaining to a user how the drape 402 is to be unfolded to cover all surfaces of the prep table 401 and surrounding areas. In FIG. 4B, the drape 402 is partially unfolded over most of the upper surfaces of the lower shelf 401a and waste receptacle 416. The drape 402 includes fabric portions 402b (e.g., pockets, hand slots, etc.) that the user may use to assist him/her in unfolding the drape 402 over the table 401. In FIG. 4C, the drape 402 is unfolded fully over the second shelf 401b so that the upper surfaces of shelf 401 are fully covered by drape 402. Further details regarding the prep or back-table drape are disclosed in U.S. Patent Application Publication No. 2013/0186413A1, entitled Surgical Drape and System having a Barrier for Preventing the Start of a Surgical Procedure and Methods for Using Same, published to Applicant on Jul. 25, 2013 and U.S. Patent Application Publication No. 2014/0261457A1, entitled Apparatus and Method Pertaining to a Multi-Tier Back-Table Drape, published to Applicant on Sep. 18, 2014, which are incorporated herein by reference in their entirety. In a preferred form, however, the drape 402 includes integral zone markers identifying and distinguishing between the first zone (e.g. tray or prep table Zone One 420) and the second zone (e.g., discard zone or waste receptacle Zone Two 430), which the camera 410 can detect in order to track instruments/items as they are moved from one zone to another. While the embodiment illustrated in FIGS. 4A-C comprises two zones, it should be understood that the system or apparatus 400 could be configured with additional zones similar to those discussed above (e.g., surgical arena zone, missing zone, etc.).

Figure 5:
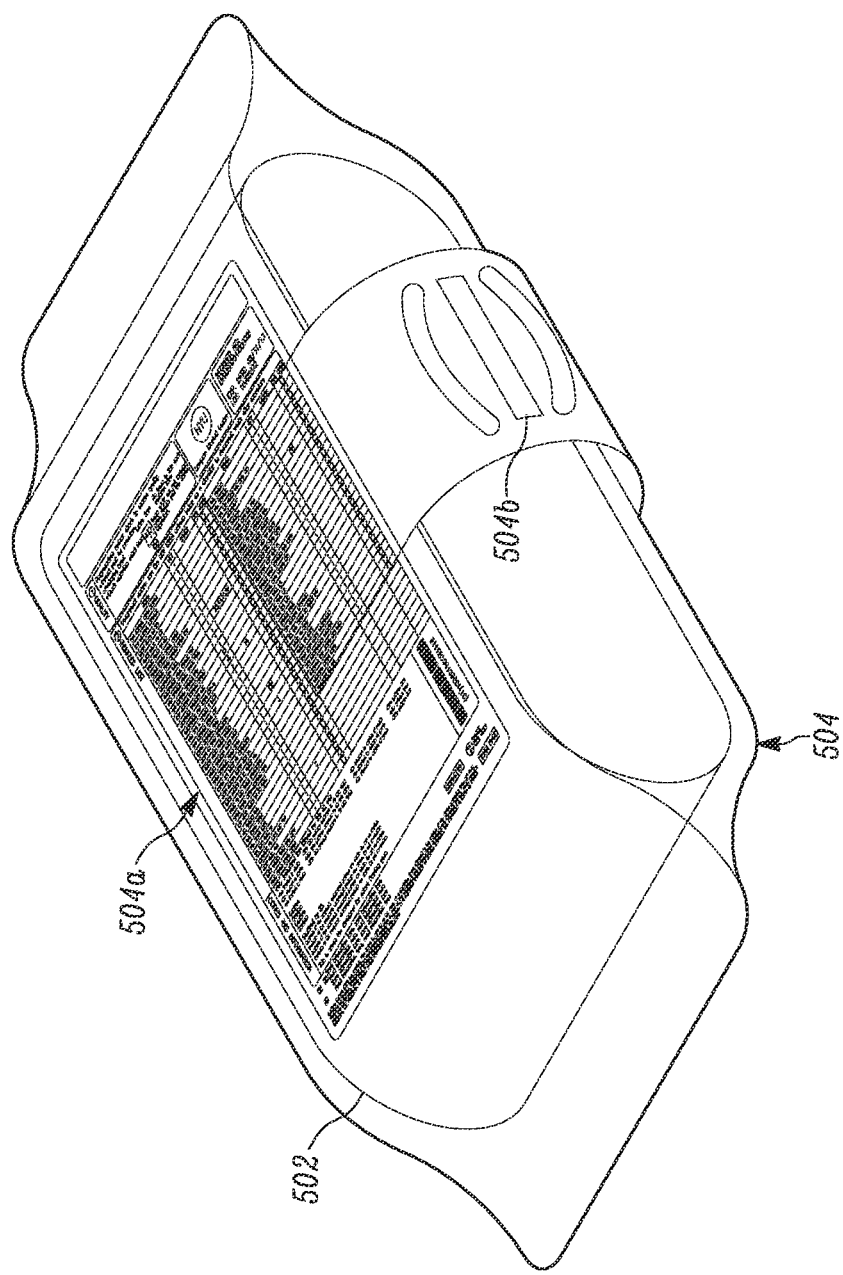
FIG. 5 is a perspective view of a custom procedure kit in accordance with embodiments of the invention and having indicia for indicating the contents of the kit and for the medical personnel to note what items have been used from same.

Turning now to FIG. 5, there is illustrated a procedural kit 504 in accordance with other embodiments of the invention. In a preferred form, the kit 504 is customized for a particular procedure and contains instruments/items that have instrument markers (like those discussed above) for use with systems or apparatus like those disclosed herein. The instruments are wrapped in a drape 502 which can be removed from the kit 504 and opened similar to drape 402 discussed with respect to FIGS. 4A-C. Once removed, the drape 502 can be unfolded as instructed and the sterilized instruments will be positioned on the prep zone of the drape, so that they tracking system or apparatus the kit 504 is used with can begin tracking movement of the instruments from zone to zone. As illustrated in FIG. 5, the kit preferably has an itemized list 504a of the kit contents on the outside of the kit 504 and has a handle 504b by which the kit can be carried and transported. Since the kit can be modified based on the particular procedure, there may be extra items that are not included in the kit and this can be denoted by leaving the quantity column blank on listing 504a for that item. Similarly, items that are not used during the medical procedure can be noted on the outer packaging that they were not used as a means for confirming that the instrument/item has not been used and, thus, is not missing. Additional details on such customized kits can be found in U.S. Patent Application Publication No. 2014/0021087A1, entitled Custom Procedure Kit, published to Applicant on Jan. 23, 2014, which is incorporated herein by reference in its entirety.

Figure 6:
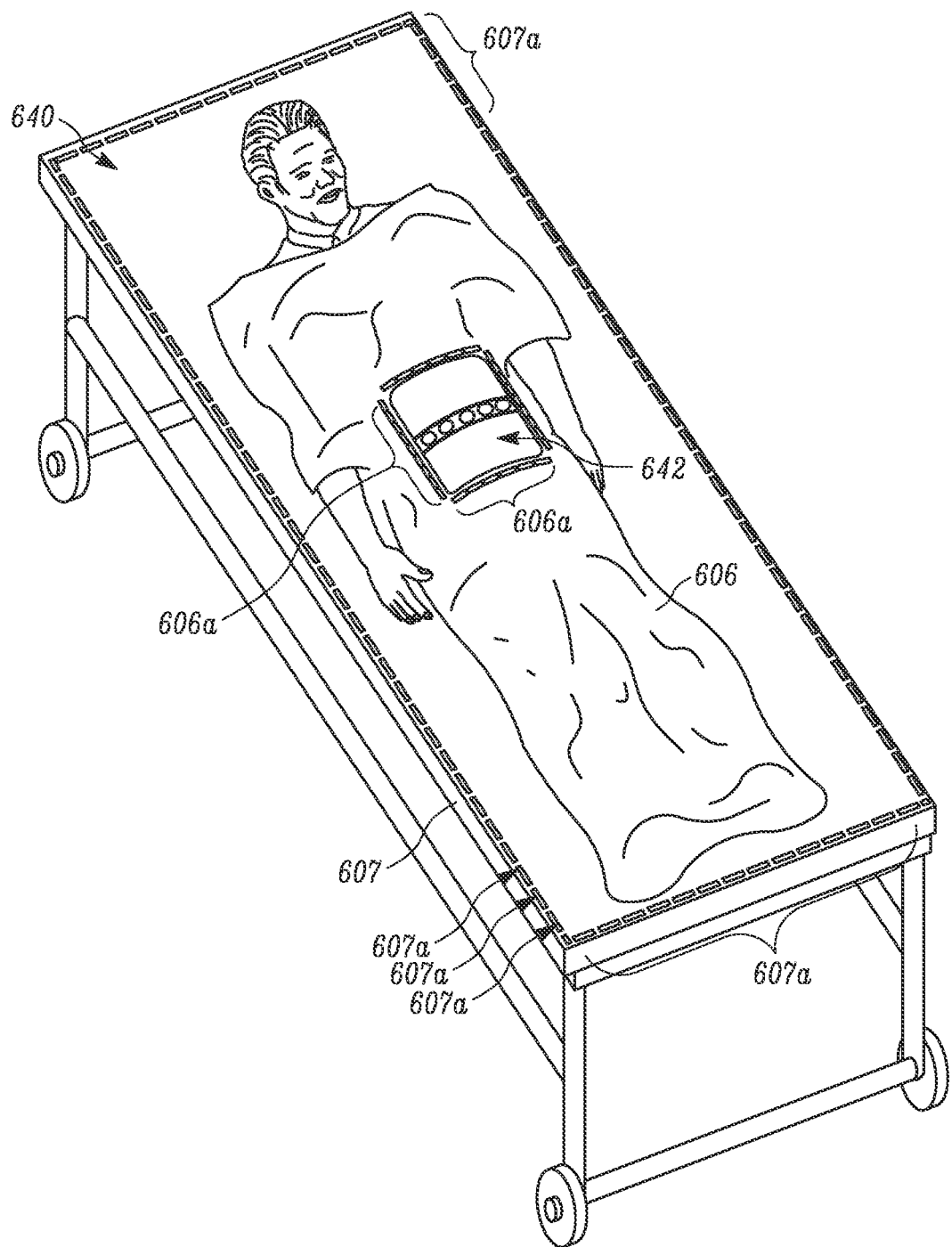
FIG. 6 is a perspective view of a patient support and surgical drape in accordance with other embodiments of the invention and having machine detectable indicia for defining boundaries of the procedural area to assist in tracking items used during the procedure and identifying where these items may be found.

FIG. 6 illustrates an exemplary patient support 607 and drape 606 in accordance with other embodiments of the invention. The patient support 607 may be a number of different patient support items, such as a bed, gurney, exam table, chair, wheelchair or the like. In the form shown, support 607 is an operating table and includes computer detectable indicia, such as zone markers 607a which tracking systems or apparatus like those discussed above can detect and use to identify the operating table boundary as a zone. For example, the tracking system or apparatus may use the markers 607a to define the operating arena zone 640 which is similar to Zone Three 140 discussed above in FIG. 1B. In some forms, the markers 607a will be integrated into the support 607 so that medical personnel do not have to worry about disturbing or damaging these items when moving patients on and off the support 607. For example, the markers 607a may be molded into the surface of the support 607. In other forms, however, the zone markers 607a may be attached to the support 607 by different means (e.g., fasteners such as screws, bolts, rivets, clasps, clamps, adhesives, hook and loop connectors, thread, welds, etc.). The zone markers 607a can be connected to support 607 so that they can be removed and replaced, or alternatively, a permanent connection may be used between the marker 607a and support 607.

In addition to the patient support 607 having zone markers 607a, the patient drape 606 illustrated in FIG. 6 may also include computer detectable indicia such as zone markers 606a. In a preferred form, drape zone markers 606a are positioned around the surgical site so that tracking systems or apparatus like those discussed herein can detect the drape markers 606a and use them to identify a surgical site zone 642 which is located within the surgical arena 640. As with the patient support markers 607a, patient drape markers 606a may be connected to the drape 606 in a variety of ways and may either be connected in a manner that makes the markers 606a permanently affixed to drape 606 or alternatively in a manner that allows them to be removably attached. In some instance, the drape 606 is designed to allow the drape markers 606a to be removed and reattached in a manner desired by the medical personnel so that the medical personnel can customize the size and shape of the surgical site zone 642 to the specific patient and/or procedure being performed. For example, in some forms, the drape 606 and drape markers 606a are connectable to one another via a releasable adhesive or a hook and loop type connection so that the markers 606a can be readily moved and/or repositioned as desired. This type of configuration may allow a generic patient drape to be used rather than requiring specific drapes for specific procedures because the medical personnel can position the drape markers 606a wherever they need to for the procedure being performed. However, in other instances, it may be desirable to require specific drapes for specific procedures as this helps ensure the procedure will be performed correctly (e.g., helps ensure the procedure will be performed in the correct spot, on the correct appendage, on the correct side, etc.).

The ability to define a smaller surgical site zone 642 within the operating arena zone 640 gives the tracking systems or apparatus discussed herein further functionality and ability to track items and alert medical personnel if an instrument/item is approaching the surgical site zone 642 that should not be approaching that zone. For example, if an already used and discarded instrument is picked-up and brought back toward the surgical site zone 642 and shouldn't be, the tracking systems or apparatus can issue an alarm to alert medical personnel to stop this from happening. Having such extra zones can also provide more surgical science data that can be collected and studied to further improve procedures and define best practices. For example, extra zones allow further tracking of what medical personnel did throughout a procedure and, thus, provides greater data to study situations that go right and those that go wrong.

In addition to the systems and apparatus discussed herein, it should be understood that numerous methods are also disclosed herein. For example, other uses can be made of the data collected via such tracking systems and apparatus. In some instances, the data may be maintained in a database form and access to same may be provided to others either for free or for fee. Entities that likely would want access to such data include insurers, medical schools, institutions performing evaluations of their own staff and procedures, researchers, suppliers of medical equipment used in such procedures, and the like. In some forms, insurers may even utilize the data collected via these systems or apparatus to help set insurance premiums and to help setup educational presentations to teach their clients best practices to minimize risk in performing various procedures.

In another example, a method for confirming proper medical procedure is disclosed herein which comprises providing a medical instrument tracking system for continuous tracking of medical instruments during a medical procedure, continuously tracking the medical instruments during the medical procedure, and alerting medical personnel when the medical instrument tracking system detects a medical instrument being used incongruous to a predetermined order of use for the medical procedure.

In still another example, a method of utilizing surgical analytics is disclosed herein comprising providing a medical procedure tracking system for continuous tracking of medical procedure analytics, continuously tracking the medical procedure analytics, utilizing the medical procedure analytics to perform at least one of the following tasks: (a) establishing a preferred medical procedure process to be followed for a specific medical procedure; (b) identifying a preferred procedural course of action for a patient based on specific details relating to that particular patient; (c) customizing a medical procedure kit for a particular medical procedure; (d) customizing a medical procedure kit for a specific patient; and/or (e) identifying a particular medical personnel's preferred medical procedure process and alerting other medical personnel to same.

Thus, it should be understood that numerous methods, systems and apparatus are disclosed herein for improving medical procedures and tracking medical instruments (or items). For example, an apparatus for tracking medical instruments throughout a procedure is disclosed herein having a single camera for tracking movement and/or detecting position of a plurality of medical instruments during a medical procedure as at least one of the plurality of medical instruments is moved between multiple zones at least including a first prep zone and a second procedure zone, a controller connected to and collecting images from the camera, and a display in electrical communication with the controller and/or the camera for displaying medical instrument data pertaining to the movement and/or position of the plurality of medical instruments.

In some forms, the apparatus for tracking medical instruments throughout a procedure includes an alarm for indicating at least one of the following alarm conditions: a medical instrument missing from all of the physical zones; a medical instrument detected in an undesired zone; a medical instrument detected in a zone for too long of a time period; a medical instrument moved out of a predetermined order established for the medical procedure involved; and/or a medical instrument moved out of a predetermined order established for the medical personnel involved. The alarm may be at least one of: an audible alarm; a visual alarm; and/or a tactile or haptic alarm. In a preferred form, the alarm is both an audible alarm and a visual alarm, the audible alarm being a speaker emitting an announcement announcing that at least one of the plurality of medical instruments has gone missing and the visual alarm is a flashing indicator on the display identifying the at least one of the plurality of medical instruments that has gone missing.

The systems or apparatus disclosed herein may include a controller and/or display having a user interface for suspending or delaying the alarm. In a preferred form, the user interface not only suspends or delays the alarm, but causes the display to display additional information relating to the alarm condition including at least one of a medical instrument position, location, velocity or speed of travel, vector or direction of travel, telemetry and/or instrument marker data.

The systems or apparatus herein also include a plurality of medical instruments each having an instrument marker and the controller of the system or apparatus is capable of tracking movement and/or detecting position of the plurality of medical instruments from their respective instrument markers. The instrument markers may include a machine readable marking comprising at least one of: a bar code; a RFID sensor; a UPC, EAN or GTIN; an alpha, numeric or alpha-numeric sequential marking; and/or an easy coding scheme that is readily identifiable by a human for redundant checking purposes. In some forms, the easy coding scheme includes a sequence of easily followed numbers, letters, and/or symbols (e.g., 1, 2, 3, 4 . . . ; 0001, 0010, 0100, 1000 . . . ; a, b, c, d . . . ; aaaa, aaab, aaac, aaad . . . ; red house, orange house, yellow house, green house . . . ; hand with 1 finger raise, hand with 2 fingers raise, hand with 3 fingers raise, hand with four fingers raised . . . ; etc.).

In some forms, the instrument marker is a two-dimensional (2D) barcode or a three-dimensional (3D) barcode machine readable from first and second angles with the first and second angles being greater than thirty degrees (30°) apart. In a preferred form, the instrument marker and controller interact as an orientation, position or angle agnostic system that is capable of tracking movement and/or detecting position of the plurality of medical instruments via the instrument marker regardless of what orientation, position or angle each medical instrument or instrument marker is in at any given time. In other forms, the instrument marker is a two-dimensional (2D) barcode or a three-dimensional (3D) barcode machine readable from an angle that is at least plus or minus thirty degrees)(±30° from normal to the instrument marker. Preferably, the instrument marker is hydrophobic to improve machine readability of the instrument marker (e.g., by being hydrophobic, the marker is self-clearing to ensure it will be detectable by the tracking system or apparatus). In still other forms, the instrument marker is formed on the medical instrument via etching, engraving, embossing, carving, molding, stamping, pressing, painting, printing, or vapor deposition.

In addition to instrument markers, there are disclosed herein machine detectable zone markers for delineating physical zones in the procedure area. In some forms, the machine detectable zone markers have first and second sides, with machine readable information on the first side and a fastener on the second side for fastening the machine detectable zone markers to a surface, the fastener including at least one of: an adhesive; a hook or loop fastener portion; a clasp or clamp; a zipper; and/or a thread. In preferred forms, the machine detectable zone markers are machine readable markings and hydrophobic to improve machine readability of the zone markers. The machine detectable zone markers may include a machine readable marking having at least one of: a bar code; a RFID sensor; a UPC, EAN or GTIN; an alpha, numeric or alpha-numeric sequential marking and/or an easy coding scheme that is readily identifiable by a human for redundant checking purposes. In some forms, the zone markers are formed on medical drapes or coverings for at least one of a surgical instrument table, patient, operating table or patient support, surgical equipment, and/or waste container.

The system or apparatus preferably includes a camera that both continually tracks movement and detects position of the plurality of medical instruments and the system or apparatus has a display that displays specific data pertaining to both the spatial movement and position of the plurality of medical instruments. In some forms, the specific data pertaining to spatial movement includes tracking at least two of a x coordinate, a y coordinate and/or a z coordinate of the at least one of the plurality of medical instruments and the specific data pertaining to location includes an identification of what zone the at least one of the plurality of medical instruments is currently located. The controller may use the camera to track medical instrument data including one or more of location, velocity or speed of travel, vector or direction of travel, and/or telemetry. In preferred forms, the controller uses the medical instrument data to provide an improved predictive analysis of where a missing medical instrument is likely to be should one of the plurality of medical instruments go missing.

The systems or apparatus may include a first zone where instruments are initially positioned prior to procedure and a second zone where instruments are positioned post procedure. In some forms, a third discard zone may also be included and tracked via the system or apparatus.

The system or apparatus will also include a user interface for locating a missing medical instrument from the plurality of medical instruments. Preferably, the user interface is at least one graphical user interface located on the display that, when actuated, the controller displays on the display an image or video of the missing medical instrument prior to the missing medical instrument going missing to assist with locating the missing medical instrument. The controller may be configured such that a single actuation of the at least one graphical user interface allows video of the missing medical instrument to be pulled-up on the display and queued up to a period of time at or near when the missing medical instrument went missing which a user can review and replay as desired. In some forms, the system or apparatus stores video into local or remote memory storage that a user can access for replay to either review a procedure or track any of the plurality of medical instruments used during the procedure.

In some forms, the system or apparatus is configured to be a medical instrument retention alert system and includes an alarm for alerting medical personnel when a medical instrument from the plurality of medical instruments has not been accounted for or is still detected in the procedure zone. If desired, the controller may further disable the apparatus from being used for any other function until the medical instrument from the plurality of medical instruments has been accounted for or removed from the procedure zone.

In other embodiments disclosed herein, a retained object system for tracking medical instruments throughout a procedure is disclosed having: a camera for monitoring a plurality of physical regions and continuously tracking movement or detecting position of a plurality of medical instruments throughout a medical procedure as at least some of the plurality of medical instruments are moved between physical regions at least including a first pre-procedure region, a second procedure region and third post-procedure region; a computer connected to the camera and collecting images from the camera; and a display in electrical communication with the computer and/or camera for displaying medical instrument data pertaining to the movement or position of the plurality of medical instruments as well as images of the physical regions.

In yet other embodiments, an apparatus for tracking medical instruments is disclosed herein having: a medical tracking device having a camera, a display and a control circuit with a non-transitory computer readable memory storing a set of instructions executable by the control circuit and configured to cause the control circuit to perform the steps of: (a) continuously tracking at least one of a plurality of medical instruments via the camera; and (b) automatically updating the display with current information regarding the position or location of the at least one of a plurality of medical instruments.

In still further embodiments, procedure drape kit is disclosed having a surgical drape having instructions for unfolding the drape in a preferred order of steps, and markers connected to the surgical drape to define at least one zone, with the at least one zone being at least one of a pre-surgical procedure zone, a surgical procedure zone, a post-surgical procedure zone.

In other embodiments, a procedure prep table is disclosed herein comprising a table having a pre-procedure area and a post-procedure area, and markers defining a general boundary of the pre-procedure area and the post-procedure area so that a medical instrument tracking device can track medical instruments as medical instruments are passing from the pre-procedure area to the post-procedure area.

In still other embodiments, a patient support is disclosed herein having a patient support having a patient support area, and markers connected to the patient support for defining a general boundary of the patient support area so that a medical instrument tracking device can track medical instruments as the medical instruments pass in and out of the patient support area.

In other embodiments, an apparatus for monitoring medical procedures and tracking the equipment used therein is disclosed herein comprising: a camera for creating images or video of a medical procedure and tracking the equipment used therein; a controller coupled to the camera for collecting the images or video from the camera and storing the collected images or video either in local memory storage or remote memory storage; and a display coupled to the controller for displaying the collected images or video from the camera and having a user interface that allows a user to review the collected images or video to monitor at least a portion of the medical procedure or the tracked equipment used therein.

In some forms, the user interface includes features for allowing the user to rewind, fast-forward, play and pause the collected images or video. The collected images or video may be stored on remote memory storage accessible via a network, and the apparatus may further include a remote display device located out of the vicinity of the camera that a user can use to access the collected images or video on the remote memory storage via the network to monitor at least a portion of the medical procedure or the tracked equipment used therein.

In yet other embodiments, an item tracking system is disclosed herein having a plurality of items, a camera for tracking the plurality of items, and a plurality of item markers each positioned on one of the plurality of items to allow the plurality of items to be tracked, the plurality of item markers and camera operating as an orientation agnostic system that allows the plurality of items to be tracked regardless of what position or orientation the plurality of items are in at any given time during a time period that the plurality of items are being tracked by the item tracking system.

In some forms, the item tracking apparatus may include a controller that uses the camera to track item data including one or more of location, velocity or speed of travel, vector or direction of travel, and/or telemetry. The controller may use the item data to provide an improved predictive analysis of where a missing item is likely to be should one of the plurality of items go missing.

This detailed description refers to specific examples in the drawings and illustrations. These examples are described in sufficient detail to enable those skilled in the art to practice the inventive subject matter. These examples also serve to illustrate how the inventive subject matter can be applied to various purposes or embodiments. Other embodiments are included within the inventive subject matter, as logical, mechanical, electrical, and other changes can be made to the example embodiments described herein. Features of various embodiments described herein, however essential to the example embodiments in which they are incorporated, do not limit the inventive subject matter as a whole, and any reference to the invention, its elements, operation, and application are not limiting as a whole, but serve only to define these example embodiments. This detailed description does not, therefore, limit embodiments of the invention, which are defined only by the appended claims. Each of the embodiments described herein are contemplated as falling within the inventive subject matter, which is set forth in the following claims. Further, it should be understood that features of one embodiment described herein may be combined with features of other embodiments described herein in order to develop yet further embodiments and such further embodiments are contemplated within this disclosure.

What is claimed is:

1. A system for tracking medical instruments, the system comprising:
   a camera configured to capture, during the course of a medical procedure, sequential images of a procedure area that includes a plurality of medical instruments disposed therein, each of the plurality of medical instruments including a different respective machine readable instrument marker disposed thereon;
   a controller operably connected to the camera, the controller configured to:
   identify the medical procedure being performed;
      receive each of the sequential images of the procedure area when captured by the camera;
      monitor a respective location of the plurality of medical instruments within the sequential images of the procedure area over the course of the medical procedure using the respective machine readable instrument marker disposed on each of the plurality of medical instruments, the respective location of the plurality of medical instruments including x, y, and z, coordinates within the procedure area;
      identify when the respective location of one or more of the plurality of medical instruments fails to conform to an expected location thereof, the expected location corresponding to the medical procedure identified by the controller.

2. The system of claim 1 wherein the controller is configured to identify the medical procedure being performed by receiving user input.

3. The system of claim 1 wherein the controller is configured to identify the medical procedure being performed by accessing electronic medical records linked to the controller.

4. The system of claim 1 wherein the controller is configured to identify when the respective location of one or more of the plurality of medical instruments fails to conform to an expected location thereof by:
   in either order, recalling an expected order of sequence for the plurality of medical instruments from a memory based on the identity of the medical procedure, and identifying a current ordering of the plurality of medical instruments from the respective location of the medical instruments within the sequential images of the procedure area;
   comparing the expected order of sequence to the current ordering of the plurality of medical instruments; and
   determining that one or more of the plurality of medical instruments fails to conform to the expected location thereof when the current ordering of the plurality of medical instruments fails to match the expected order of sequence.

5. The system of claim 4 wherein fy the expected order of sequence for the plurality of medical instruments is generated based on information gathered from prior executions of medical procedure and then stored in the memory.

6. The system of claim 1 wherein the controller is configured to identify when the respective location of one or more of the plurality of medical instruments fails to conform to an expected location thereof by:
   identifying a plurality of zones of the procedure area using the sequential images of the procedure area;
   tracking the respective location of the medical instruments relative to the plurality of zones over the course of the medical procedure; and
   determining that one or more of the plurality of medical instruments fails to conform to the expected location thereof when one or more of the plurality of medical instruments is missing from an associated one of the plurality of zones as indicated by the medical procedure identified by the controller.

7. The system of claim 6 wherein the controller is configured to identify the plurality of zones from the sequential images of the procedure area by detecting, in the sequential images of the procedure area, one or more zone markers deployed in the procedure area.

8. The system of claim 1 wherein the controller is configured to identify when the respective location of one or more of the plurality of medical instruments fails to conform to an expected location thereof by:
   identifying a plurality of zones of the procedure area using the sequential images of the procedure area;
   tracking the respective location of the medical instruments relative to the plurality of zones over the course of the medical procedure; and
   determining that one or more of the plurality of medical instruments fails to conform to the expected location thereof when one or more of the plurality of medical instruments is detected in a correspondingly undesired one the plurality zones as indicated by the medical procedure identified by the controller.

9. The system of claim 1 wherein the controller is configured to identify when the respective location of one or more of the plurality of medical instruments fails to conform to an expected location thereof by:
   identifying a plurality of zones of the procedure area using the sequential images of the procedure area;

tracking the respective location of the medical instruments relative to the plurality of zones over the course of the medical procedure; and determining that one or more of the plurality of medical instruments fails to conform to the expected location thereof when one or more of the plurality of medical instruments is detected in one the plurality of zones for longer than a predeterminer period of time associated with the medical procedure identified by the controller.

10. The system of claim 1 wherein the controller is configured to identify when the respective location of one or more of the plurality of medical instruments fails to conform to an expected location thereof by determining that one or more of the plurality of medical instruments are moving towards a body portion of a patient that is not associated with the medical procedure identified by the controller.

11. The system of claim 1 wherein the controller is further configured to initiate an alarm in response to determining that one or more of the plurality of medical instruments fails to conform to the expected location thereof.

12. The system of claim 1 further comprising a display operably connected to the controller, wherein the controller is configured to direct the display to display information relating to the respective location of the medical instruments within the sequential images of the procedure area over the course of the medical procedure.

13. The system of claim 1 further comprising a scanner, the scanner configured to scan the procedure area to locate the one or more of the plurality of medical instruments for which the respective location fails to conform to the expected location thereof.

14. The system of claim 13 wherein the scanner is configured to provide an alert when the scanner is proximate to the one or more of the plurality of medical instruments for which the respective location fails to conform to the expected location thereof.

15. The system of claim 1 wherein the controller comprises a remote central controller located outside of the procedure area and coupled to the camera via a network.

16. A method for tracking medical instruments, the method comprising:
identifying a medical procedure being performed via a controller;
capturing, via a camera during the course of a medical procedure, sequential images of a procedure area that includes a plurality of medical instruments disposed therein, each of the plurality of medical instruments including a different respective machine readable instrument marker disposed thereon;
receiving the sequential images of the procedure area at the controller;
monitoring, via the controller, a respective location of the medical instruments within the sequential images of the procedure area over the course of the medical procedure using the respective machine readable instrument marker disposed on each of the plurality of medical instruments, the respective location of the plurality of medical instruments including x, y, and z, coordinates within the procedure area; and
identifying, via the controller, when the respective location of one or more of the plurality of medical instruments fails to conform to an expected location thereof, the expected location being a function of the medical procedure as identified by the controller.

17. The method of claim 16 wherein identifying, via the controller, when the respective location of one or more of the plurality of medical instruments fails to conform to an expected location thereof includes:
in either order, recalling an expected order of sequence for the plurality of medical instruments from a memory based on the identity of the medical procedure, and identifying a current ordering of the plurality of medical instruments from the respective location of the medical instruments within the sequential images of the procedure area;
comparing, via the controller, the expected order of sequence to the current ordering of the plurality of medical instruments; and
determining, via the controller, that one or more of the plurality of medical instruments fails to conform to the expected location thereof when the current ordering of the plurality of medical instruments fails to match the expected order of sequence.

18. The method of claim 16 wherein identifying, via the controller, when the respective location of one or more of the plurality of medical instruments fails to conform to an expected location thereof includes:
identifying, via the controller, a plurality of zones of the procedure area using the sequential images of the procedure area;
tracking, via the controller, the respective location of the medical instruments relative to the plurality of zones over the course of the medical procedure; and
determining, via the controller, that one or more of the plurality of medical instruments fails to conform to the expected location thereof when one or more of the plurality of medical instruments is missing from an associated one of the plurality of zones as indicated by the medical procedure identified by the controller.

19. The method of claim 16 wherein identifying, via the controller, when the respective location of one or more of the plurality of medical instruments fails to conform to an expected location thereof includes:
identifying, via the controller, a plurality of zones of the procedure area using the sequential images of the procedure area;
tracking, via the controller, the respective location of the medical instruments relative to the plurality of zones over the course of the medical procedure; and
determining, via the controller, that one or more of the plurality of medical instruments fails to conform to the expected location thereof when one or more of the plurality of medical instruments is detected in a correspondingly undesired one the plurality zones as indicated by the medical procedure identified by the controller.

20. The method of claim 16 wherein identifying, via the controller, when the respective location of one or more of the plurality of medical instruments fails to conform to an expected location thereof includes:
identifying, via the controller, a plurality of zones of the procedure area using the sequential images of the procedure area;
tracking, via the controller, the respective location of the medical instruments relative to the plurality of zones over the course of the medical procedure; and determining, via the controller, that one or more of the plurality of medical instruments fails to conform to the expected location thereof when one or more of the plurality of medical instruments is detected in one the plurality of zones for longer than a predeterminer period of time associated with the medical procedure identified by the controller.

\* \* \* \* \*